United States Patent
Chosa et al.

(10) Patent No.: US 6,452,030 B1
(45) Date of Patent: Sep. 17, 2002

(54) BETAINE COMPOUND AND PROCESS FOR PRODUCTION THEREOF

(75) Inventors: Junichi Chosa, Suita; Takashi Tomita, Toyonaka, both of (JP); Malcolm Andrew Kelland, Rφyneberg (NO)

(73) Assignee: Nippon Shokubai Co., Ltd., Osaka (JP)

( * ) Notice: Subject to any disclaimer, the term of this patent is extended or adjusted under 35 U.S.C. 154(b) by 8 days.

(21) Appl. No.: 09/714,259

(22) Filed: Nov. 17, 2000

(30) Foreign Application Priority Data

Nov. 17, 1999 (JP) .......................................... 11-326708

(51) Int. Cl.$^7$ .................... C07C 237/00; C07C 205/00; C07C 213/00
(52) U.S. Cl. ........................ 554/52; 560/155; 562/553; 564/292
(58) Field of Search ........................ 560/155; 564/292; 562/553; 554/52

(56) References Cited

U.S. PATENT DOCUMENTS

| | | | | |
|---|---|---|---|---|
| 3,265,719 A | * | 8/1966 | Cowen et al. | 554/110 |
| 3,706,562 A | * | 12/1972 | Herz et al. | 430/446 |
| 3,838,075 A | * | 9/1974 | Dietrich et al. | 504/360 |
| 4,426,445 A | * | 1/1984 | Minamizono et al. | 430/599 |
| 4,470,918 A | * | 9/1984 | Mosier | 252/77 |
| 4,883,917 A | * | 11/1989 | Smith et al. | 564/292 |

FOREIGN PATENT DOCUMENTS

| GB | 1 419 202 | 12/1975 |
|---|---|---|
| GB | 2 076 983 A | 12/1981 |
| JP | 5032600 | 2/1993 |
| JP | 5294905 | 11/1993 |
| WO | WO 99/13197 | 3/1999 |

* cited by examiner

Primary Examiner—Alan L. Rotman
Assistant Examiner—T. Victor Oh
(74) Attorney, Agent, or Firm—Connolly Bove Lodge & Hutz LLP

(57) ABSTRACT

This invention provides a hydroxyl group-containing betaine compound and a long-chain alkyl group-containing betaine compound, both of which are highly biodegradable and useful as surfactants, bactericides, antistatic agents, softening agents, rust inhibitors, resin modifiers, synthetic intermediates, etc. The invention further provides processes for producing such betaine compounds.

The hydroxyl group-containing betaine compound mentioned above can be represented by the following general formula (1)

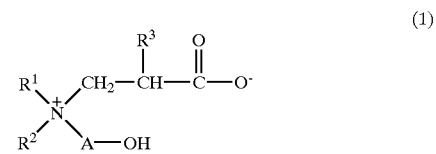

wherein $R^1$ and $R^2$ maybe the same or different and each represents a hydrogen atom, a $C_{1-8}$ hydrocarbon group or a $C_{1-8}$ hydrocarbon group having a hydroxyl group, exclusive of the case in which both of $R^1$ and $R^2$ respectively represent a hydrogen atom; in case neither $R^1$ nor $R^2$ represents a hydrogen atom, $R^1$ and $R^2$ may be joined to each other through a single bond or through at least one kind of element selected from the group consisting of O, S and N; $R^3$ represents a hydrogen atom, a methyl group or a hydroxymethyl group; A represents a hydrocarbon group of 2~25 carbon atoms.

6 Claims, 22 Drawing Sheets

BETAINE COMPOUND AND PROCESS FOR PRODUCTION THEREOF

FIELD OF THE INVENTION

The present invention relates to a hydroxyl group-containing betaine compound, a long-chain alkyl group-containing betaine compound, and processes for producing said compounds.

PRIOR ART

The betaine compound has both a cationic group and an anionic group within its molecule and, because of this structural feature, has been attracting attention as an. amphoteric surfactant in recent years. Amphoteric surfactants have many beneficial properties such as exceptionally high resistance to hard water and low toxicity, and are used with advantage in various applications such as surfactants, bactericides, antistatic agents, softening agents, rust inhibitors and so on.

Japanese Kokai Publication Hei-5-32600 discloses a process for producing a betaine compound which comprises reacting an aliphatic primary amine with a quaternary ammonium compound having a defined structure at $6 \leq pH < 8$ and further reacting the reaction product with a defined halogenated lower carboxylic acid at $6 \leq pH < 8$. The betaine compound produced by this process has foaming and detergent properties so that it can be used as a surfactant for hair and body cleansing. However, in order that a variety of properties other than foaming and detergent properties may be imparted to such a betaine compound to thereby expand its scope of application, a further investigation into related compounds was needed.

Japanese Kokai Publication Hei-5-294905 discloses a carbobetaine compound and a process for its production. This process for producing a carbobetaine compound comprises reacting a defined amino compound with a defined halogen-containing salt. The carbobetaine compound obtainable by this process has an emolient action on the hairs and skin so that it finds application as an emolient in hair care and skin care products. However, with regard to such carbobetaine compound, too, further investigations are needed into related compounds in order to impart a variety of properties other than emolient activity for an expanded scope of application.

SUMMARY OF THE INVENTION

The present invention, developed in light of the above state of the art, has for its object to provide a hydroxyl group-containing betaine compound and a long-chain alkyl group-containing betaine compound, both of which are highly biodegradable and useful as surfactants, bactericides, antistatic agents, softening agents, rust inhibitors, resin-modifying agents, and synthetic intermediates, as well as processes for producing said compounds.

The present invention relates to a hydroxyl group-containing betaine compound of the following general formula (1):

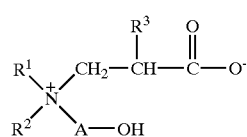

(1)

wherein $R^1$ and $R^2$ may be the same or different and each represents a hydrogen atom, a $C_{1-8}$ hydrocarbon group or a $C_{1-8}$ hydrocarbon group having a hydroxyl group, exclusive of the case in which both of $R^1$ and $R^2$ respectively represent a hydrogen atom; in case neither $R^1$ nor $R^2$ represents a hydrogen atom, $R^1$ and $R^2$ may be joined to each other through a single bond or through at least one kind of element selected from the group consisting of O, S and N; $R^3$ represents a hydrogen atom, a methyl group or a hydroxymethyl group; A represents a $C_{2-25}$ hydrocarbon group.

In a further aspect, the present invention relates to a process for producing a hydroxyl group-containing betaine compound of the following general formula (1):

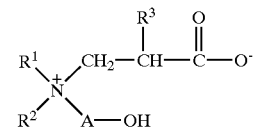

(1)

wherein $R^1$, $R^2$, $R^3$ and A are respectively as defined above, which comprises a step of reacting a β-alanine derivative of the following general formula (2):

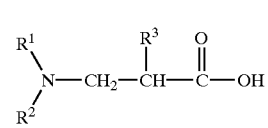

(2)

wherein $R^1$, $R^2$ and $R^3$ are respectively as defined above, with a monooxirane compound.

In a further aspect, the present invention relates to a long-chain alkyl group-containing betaine compound of the following general formula (3):

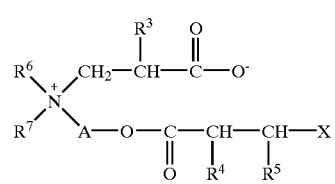

(3)

wherein $R^6$ and $R^7$ maybe the same or different and each represents a hydrogen atom or a $C_{1-8}$ hydrocarbon group, exclusive of the case in which both of $R^6$ and $R^7$ respectively represent a hydrogen atom; in case neither $R^6$ nor $R^7$ represents a hydrogen atom, $R^6$ and $R^7$ may be joined to each other through a single bond or through at least one kind of element selected from the group consisting of O, S and N; $R^3$ and A are as defined above; $R^4$ and $R^5$ are such that whichever one of them represents a hydrogen atom and the other represents a $C_{5-30}$ hydrocarbon group; X represents a hydrogen atom or —COOM, where M represents a hydrogen atom, a metal atom or an ammonium group.

In a still further aspect, the present invention relates to a process for producing a long-chain alkyl group-containing betaine compound of the following general formula (3):

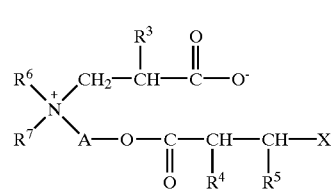

(3)

wherein $R^6$, $R^7$, $R^3$, A, $R_4$, $R_5$ and X are respectively as defined above, which comprises a step of reacting a hydroxyl group-containing betaine compound of the following general formula (6):

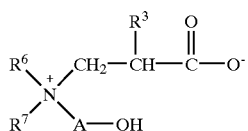
(6)

wherein $R^6$, $R^7$, $R^3$ and A are respectively as defined above, with either a long-chain alkyl group-containing carboxylic acid of the following general formula (4):

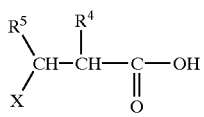
(4)

wherein $R^4$, $R^5$ and X are respectively as defined above, or a long-chain alkyl group-containing carboxylic anhydride of the following general formula (5):

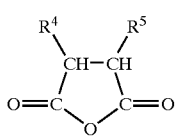
(5)

wherein $R^1$ and $R^5$ are respectively as defined above.

DETAILED DESCRIPTION OF THE INVENTION

Figure 1:
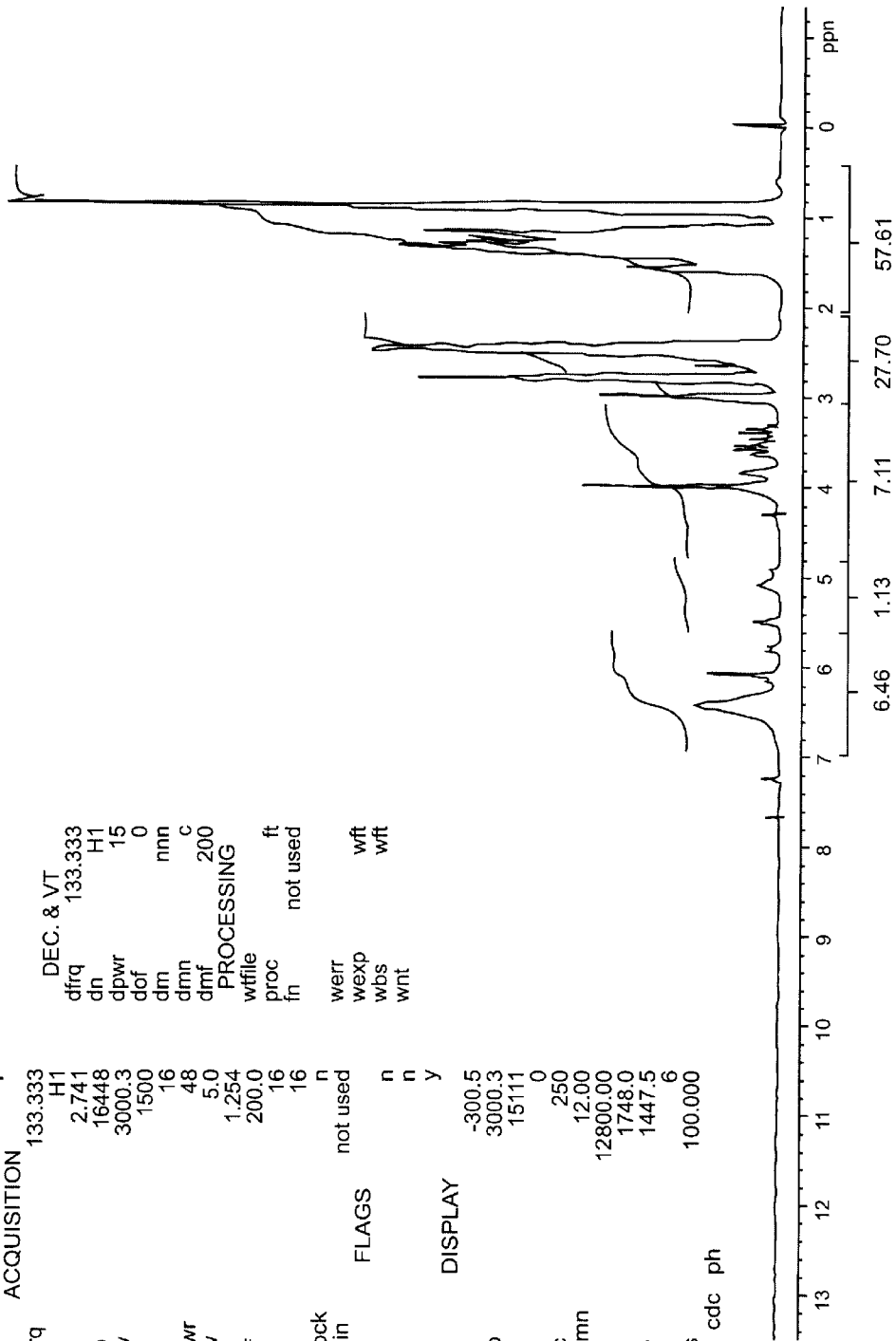
FIG. 1 is a $^1$H-nuclear magnetic resonance spectrum of the hydroxyl group-containing betaine compound 1 obtained in Example 1.

The hydroxyl group-containing betaine compound of the present invention is represented by the above general formula (1).

Referring to the above general formula (1), the $C_{1-8}$ hydrocarbon group mentioned for $R^1$ and $R^2$ is not particularly restricted and includes alkyl groups such as methyl, ethyl, propyl, isopropyl, butyl, isobutyl, pentyl, hexyl, cyclohexyl, octyl, etc. The Clad hydrocarbon group having a hydroxyl group, also mentioned for $R^1$ and $R^2$, is not particularly restricted but includes 2-hydroxyethyl, 3-hydroxypropyl, 2-hydroxypropyl, 2-hydroxybutyl, 2-hydroxyhexyl, 2-hydroxyoctyl, etc. When neither $R^1$ nor $R^2$ is a hydrogen atom, $R^1$ and $R^2$ are joined to each other through a single bond or through at least one kind of element selected from the group consisting of O, S and N, where the group involved may for example be a tetramethylene group, a pentamethylene group, a hexamethylene group, an ethyleneoxyethylene group, an ethyleneiminoethylene group or the like.

Referring, further, to the above general formula (1), the $C_{2-25}$ hydrocarbon group mentioned for A is not particularly restricted but includes a methylene group, an ethylene group, a propylene group, an isopropylene group, a butylene group, an isobutylenegroup, apentylgroup, anoctylgroup, adecylgroup, a dodecyl group, a tetradecyl group, a hexadecyl group, an octadecyl group, an eicosyl group, a docosyl group, a pentacosyl group, etc.

The hydroxyl group-containing betaine compound of the present invention has $N^+$ as the cationic group and $COO^-$ as the anionic group within its molecule and has a specific structure containing a hydroxyl group and a defined hydrocarbon group bound to said $N^+$. It is highly biodegradable and useful as a ssurfactant, an insecticide, an antistatic agent, a softening agent, a rust inhibitor, a resin modifier or a synthetic intermediate.

The method of producing the hydroxyl group-containing betaine compound of the present invention is not particularly restricted but a preferred process may for example comprise reacting a β-alanine derivative of the general formula (2) with a monooxirane compound. This process for producing a hydroxyl group-containing betaine compound also falls within the scope of the present invention. Throughout this specification, the above process is sometimes referred to as the monooxirane compound addition step.

The β-alanine derivative of the general formula (2) for use in said monooxirane compound addition step is not particularly restricted but includes the compound which can be easily synthesized by the addition reaction of an acrylic acid compound, such as (meth)acrylic acid, 2-hydroxyinethylacrylic acid or the like, to a primary or secondary amine.

The process for producing said hydroxyl group-containing betaine compound according to the present invention may includes a step of synthesizing such a β-alanine derivative of the general formula (2). In this specification, this step is sometimes referred to as the β-alanine derivative-synthesizing step.

The primary amine mentioned above is not particularly restricted but includes straight-chain or branched-chain primary alkylamines and primary hydroxyalkylamines, such as octylamine, 2-ethylhexylamine, heptylarnine, hexylamine, pentylamine, n-butylamine, isobutylamine, n-propylamine, isopropylamine, ethylamine, methylamine, 2-hydroxyethylamine, 2-hydroxypropylamine, 2-hydroxyhexylamine, 2-hydroxyoctylamine, etc. These may be used each alone or in a combination of two or more species.

The secondary amine mentioned above is not particularly restricted but includes straight-chain, branched-chain or cyclic secondary alkylamines and secondary hydroxyalkylamines, such as dimethylamine, diethylamine, di-n-propylamine, diisopropylamine, di-n-butylamine, diisobutylamine, di-n-pentylamine, methylethylamine, dihexylamine, dioctylamine, ethyleneimine, pyrrolidine, piperidine, hexamethyleneimine, morpholine, piperazine, N-methylpiperazine, di(2-hydroxy)ethylamine, di(2-hydroxy)propylamine, di(2-hydroxy)octylamine, etc. These may be used each alone or in a combination of two or more species.

Referring to this β-alanine derivative-synthesizing step, the method of mixing said acrylic acid compound with said primary or secondary amine is not particularly restricted. For example, if only for the purpose of suppressing the heat of neutralization which evolves on said mixing and facilitating temperature control, it is preferable to charge a reaction vessel with one of said reactants and add the other reactant continuously or serially. In other words, it is optional to charge the reaction vessel with the acrylic acid compound in the first place and add the primary or secondary amine thereto continuously or serially or, the other way round, charge the reaction vessel with the primary or secondary amine and then add the acrylic acid compound thereto continuously or serially.

In the above β-alanine derivative-synthesizing step, the reaction may be carried out in the absence of a solvent but, where necessary, a solvent may be employed. The use of a catalyst is not essential but a catalyst may be used for promoting the reaction or suppressing side reactions.

The solvent mentioned above is not particularly restricted as long as it does not react with the reactant acid or amine or interfere with the reaction. Thus, it includes aliphatic hydrocarbons, such as hexane, octane, etc.; alicyclic saturated hydrocarbons,Isuch as cyclohexane etc.; alicyclic unsaturated hydrocarbons, such as cyclohexene etc.; aromatic hydrocarbons, such asbenzene, toluene, xylene, etc.; ketones, such as acetone, methyl ethyl ketone, etc.; esters, such as methyl acetate, ethyl acetate, butyl acetate, etc.; halogenated hydrocarbons, such as dichlorbmethane, chloroform, carbon tetrachloride, etc.; ethers, such as diethyl ether, dioxane, dioxolane, etc.; alcohols, suchasmethanol, ethanol, isopropyl alcohol, butanol, etc.; water; amides, such as N,N-dimethylformamide etc.; sulfoxides, such as dimethyl sulfoxide etc.; and nitriles, such as acetonitrile etc. These may be used each alone or in a combination of two or more species.

The catalyst mentioned above is not particularly restricted but includes basic catalysts, such as sodium hydroxide, potassium hydroxide, calcium hydroxide, sodium methoxide, lithium methoxide, sodium ethoxide, tertiary amine compounds and quaternary ammonium compounds, among others. These may be used each alone or in a combination of two or more species.

In carrying out the β-alanine derivative-synthesizing step, a polymerization inhibitor may be used for preventing polymerization of the acrylic acid compound. The polymerization inhibitor which can be used is not particularly restricted but includes phenol type polymerization inhibitors, such as hydroquinone, methoxyhydroquinone, benzoquinone, etc.; sulfur type polymerization inhibitors, such as dilauryl-3,3'-thiodipropionate, 2-mercaptobenzimidazole, phenothiazine, etc.; and phosphorus type polymerization inhibitors, such as tris (isodecyl) phosphite, diphenylisodecyl phosphite, etc. These may be used either alone or in a combination of two or more species.

The reaction temperature for use in the above β-alanine derivative-synthesizing step is not particularly restricted but may for example be within a range not over the boiling point of the reactant acid and that of the reactant amine. In consideration of the ease with which the reaction temperature canbe controlled, more preferred temperature range is 0 to 250° C. The still more preferred range is 20 to 150° C., where the side reactions owing to excessive heating may be avoided to give the objective β-alanine derivative with high selectivity. The reaction pressure is not particularly restricted but is preferably not higher than, for example, 10 atm.

The monooxirane compound for use in the above monooxirane compound addition step is not particularly restricted but includes ethylene oxide, propylene oxide, butylene oxide, 1,2-epoxyoctane, 1,2-epoxydecane, 1,2-epoxydodecane, 1,2-epoxypentadecane, 1,2-epoxyoctadecane, 1,2-epoxyeicosane, 1,2-epoxypentacosane, etc. These may be used each alone or in a combination of two or more species.

Referring to this monooxirane compound addition step, the method of mixing the β-alanine derivative with the monooxirane compound is not particularly restricted but is preferably selected in consideration of the reactivity of the monooxirane compound, among other factors. A usually preferred method comprises charging a reaction vessel with the β-alanine derivative and adding the monooxirane compound continuously or serially, although the β-alanine derivative and monooxirane compound may be mixed together in one operation depending on reaction conditions.

Since the monooxirane compound has explosive nature, this monooxirane compound addition step is preferably carried out in an inert gas atmosphere.

The inert gas mentioned above is not particularly restricted but includes nitrogen, helium, neon and other gases, although nitrogen gas is generally employed.

When, in this monooxirane compound addition step, the reaction is conducted under elevated pressure, it is good practice to elevate the internal pressure of the reaction vessel with said inert gas in advance in order to evade the explosive range of the monooxirane compound. The degree of pressurization with said inert gas is preferably selected in consideration of the reactivity of the monooxirane compound used, the reaction temperature, and the pressure resistance of the reaction vessel used. The reaction pressure is not particularly restricted but the reaction may preferably be conducted at a pressure of not more than 10 atm.

In the monooxirane compound addition step, the reaction may be carried through in the absence of a solvent but, if necessary, a solvent can be employed. Moreover, the use of a catalyst is not essential but a catalyst may be used for the purpose of promoting the reaction and/or suppressing side reactions.

The solvent mentioned above is not particularly restricted as long as it does not interfere with the reaction, and the same solvents as mentioned hereinbefore may for example be employed. These solvents may be used each alone or in a combination of two or more species.

The catalyst mentioned above is not particularly restricted but includes the basic catalysts mentioned hereinbefore and acid catalysts such as hydrochloric acid, sulfuric acid, nitric acid, methanesulfonic acid, zeolite and so on. These may be used each alone or in a combination of two or more species.

The reaction temperature for use in the above monooxirane compound addition step is not particularly restricted but, in consideration of the ease with which the reaction temperature may be controlled, is preferably within the range of 0 to 200° C. From the standpoint of suppressing side reactions, more preferred range is 20 to 150° C. By virtue of including said monooxirane compound addition step, the process for producing a hydroxyl group-containing betaine compound according to the present invention provides a hydroxyl group-containing betaine compound of the general formula (1) with high efficiency and in good yield.

The long-chain alkyl group-containing betaine compound of the present invention is represented by the above general formula (3). Referring to the above general formula (3), the $C_{1-8}$ hydrocarbon group for $R^6$ and $R^7$; the group formed by $R^6$ and $R^7$, when neither $R^6$ nor $R^7$ is a hydrogen atom, $R^6$ and $R^7$ may be joined to each other through a single bond or through at least one kind of element selected from the group consisting of O, S and N; and the $C_{2-25}$ hydrocarbon group forA are not particularly restricted but respectively include the same specific groups as mentioned hereinbefore, among others.

In the above general formula (3), the $C_{5-30}$ hydrocarbon group for $R^4$ and $R^5$, which may have one or more fluorine or chlorine atoms substituted for its hydrogen atom or atoms, is not particularly restricted but includes straight-chain or branched-chain alkyl groups, such as octyl, nonyl, decyl, dodecyl, tetradecyl, hexadecyl, octadecyl, eicosyl, docosyl, tetracosyl, triacontyl, 2-ethylhexyl, etc.; alkenyl groups, suchasoctenyl, decenyl, dodecenyl, tetradecenyl, hexadecenyl, octadecenyl, eicosenyl, docosenyl, tetracosenyl, triacontecenyl, etc.; and groups formed as such groups are joined to each other.

In the case where X in the above general formula (3) is represented by —COOM, the long-chain alkyl group-containing betaine compound assumes the acid form when M is a hydrogen atom, i.e. X is a carboxyl group; the metal salt form when M is a metal: atom; and the ammonium salt form when M is an ammonium group.

The long-chain alkyl group-containing betaine compound of the present invention has the cationic group $N^+$, the anionic group $COO^-$ within its molecule, and has a specific structure containing a long-chain alkyl group by ester bonding and an a defined hydrocarbon group bound to said $N^+$ and, as such, it is highly biodegradable and useful as a surfactant, a bactericide, an antistatic agent, a softening agent, a rust inhibitor, a resin modifier or a synthetic intermediate.

The method of producing the long-chain alkyl group-containing betaine compound according to the present invention is not particularly restricted. A preferred process for Iproducing a long-chain alkyl group-containing betaine compound may for example be a process comprising a step of reacting said hydroxyl group-containing betaine compound of the above general formula (6) with said long-chain alkyl group-containing carboxylic acid of the above general formula (4) or the above long-chain alkyl group-containing carboxylic anhydride of the general formula (5). This process for producing said long-chain alkyl group-containing betaine compound also falls within the scope of the present invention. In this specification, the above process is sometimes referred to as the long-chain alkyl-introducing step.

The hydroxyl group-containing betaine compound of the above general formula (6) for use in said long-chain alkyl-introducing step is not particularly restricted but the compound obtainable by the above-described process for producing a hydroxyl group-containing betaine compound is used with advantage. In this connection, the process for producing a long-chain alkyl group-containing betaine compound according to the present invention preferably includes said monooxirane compound addition step.

The long-chain alkyl group-containing carboxylic acid of the general formula (4) for use in the long-chain alkyl-introducing step may be a monocarboxylic acid in which X is a hydrogen atom or a dicarboxylic acid in which X is —COOM. However, when the dicarboxylic acid is used, M is preferably a metal atom or an ammonium group. If X is a carboxyl group or an alkoxycarbonyl group of the formula —COOR (R represents a hydrocarbon group), one mole of the long-chain alkyl group-containing carboxylic acid of the general formula (4) may react with 2 moles of the hydroxyl group-containing betaine compound of the general formula (6), thus failing to give the desired long-chain alkyl group-containing betaine compound of the general formula (3) in a sufficiently high yield. The $C_{5-30}$ hydrocarbon group for $R^4$ and $R^1$ may be a saturated hydrocarbon group or an unsaturated hydrocarbon group.

The long-chain alkyl group-containing carboxylic acid of the above general formula (4) is not particularly restricted as long as it meets the above definition. Thus, it includes monocarboxylic acids, such as caprylic acid, capric acid, lauric acid, myristic acid, palmitic acid, stearic acid, behenic acid, oleic acid, linoleic acid, linolenic acid, etc.; and dicarboxylic acids, such as dodecenylsuccinic acid, tetradecenylsuccinic acid, octadecenylsuccinic acid, etc. These may be used each alone or in a combination of two or more species.

The reaction of the above hydroxyl group-containing betaine compound of the general formula (6) with the above long-chain alkyl group-containing carboxylic acid of the general formula (4) can be carried out in the manner of dehydrative condensation.

The catalyst for use in this dehydrative condensation reaction is not particularly restricted only if said catalyst is usually employed for dehydrative condensation, but includes acid catalysts, such as sulfuric acid, hydrochloric acid, nitric acid, p-toluenesulfonic acid, methanesulfonic acid, zeolite and so on. These may be used each alone or in a combination of two or more species.

The above dehydrative condensation reaction may be conducted in the absence of a solvent but, for the purpose of facilitating temperature control and removal of by product water, a suitable solvent is preferably employed.

The solvent mentioned above is not particularly restricted as long as it does. not react with the reactant hydroxyl group-containing betaine compound or long-chain alkyl group-containing carboxylic acid, nor does it otherwise interfere with the reaction, but includes the same solvents as mentioned hereinbefore. These solvents may be used each alone or in a combination of two or more species. However, alcohols, water and esters are undesirable, for these solvents take part in the reaction so that the objective long-chain alkyl group-containing betaine compound may not be obtained in good yield.

The reaction temperature for the above dehydrative condensation reaction is not particularly restricted but the reaction is preferably carried out within a temperature range not over the boiling points of the reactant hydroxyl group-containing betaine compound and long-chain alkyl group-containing carboxylic acid compound. In consideration of the ease with which the reaction temperature may be controlled, more preferred temperature range is 20 to 250° C. Still more preferred range is 50 to 200° C., where side reactions due to excessive heating may be suppressed to give the long-chain alkyl group-containing betaine compound with high selectivity. The reaction pressure is not particularly restricted but the reaction is preferably carried out at a pressure not exceeding 10 atm.

In the long-chain alkyl group-containing carboxylic anhydride of the general formula (5) for use in the above long-chain alkyl-introducing step, the $C_{5-30}$ hydrocarbon group for $R^4$ and $R^5$ may be a saturated hydrocarbon group or an unsaturated hydrocarbon group.

The long-chain alkyl group-containing carboxylic anhydride of the above general formula (5) is not particularly restricted as long as it meets the above-mentioned definition, but includes dodecenylsuccinic anhydride, tetradecenylsuccinic anhydride and octadecenylsuccinic anhydride, among others. These may be used each alone or in a combination of two or more species.

When said hydroxyl group-containing betaine compound of the general formula (6) is reacted with said long-chain alkyl group-containing carboxylic anhydride of the general formula (5), the long-chain alkyl group-containing betaine compound of the general formula (3) is an acid wherein X is carboxy.

In conducting the above reaction, a catalyst is not essential because this is a reaction of a hydroxy-containing compound with a carboxylic anhydride.

The above reaction may be conducted in the absence of a solvent but a solvent can be used where necessary.

The above solvent is not particularly restricted as long as it does not react with the reactant hydroxyl group-containing betaine compound or long-chain alkyl group-containing carboxylic anhydride, nor does it otherwise interfere with the reaction. Thus, the same specific solvents as mentioned hereinbefore can be employed. These may be used each alone or in a combination of two or more species. However, alcohols and water are not preferred, for these will react with the long-chain alkyl group-containing carboxylic anhydride.

The reaction temperature for the above reaction is not particularly restricted but is preferably not over the boiling points of the reactant hydroxyl group-containing betaine compound and reactant long-chain alkyl group-containing carboxylic anhydride. More preferred temperature range is −50 to 300° C. Still more preferred range is 0 to 200° C., where side reactions due to excessive heating may be suppressed to give the long-chain alkyl group-containing betaine compound with high selectivity. The reaction pressure is not particularly restricted but the reaction is preferably conducted at a pressure of, for example, not over 10 atm.

The process for producing a long-chain alkyl group-containing betaine compound according to the present invention may include, in the case X is —COOM in the long-chain alkyl group-containing betaine compound obtained in said long-chain alkyl group-inducing step, a step of converting M, e.g. where X is an acid, i.e. a carboxyl group, neutralizing it to form a metal salt or an ammonium salt.

By virtue of including said long-chain alkyl group-introducing step, the process for producing a long-chain alkyl group-containing betaine compound according to the present invention provides a long-chain alkyl group-containing betaine compound of the general formula (3) with high efficiency and in good yield.

The hydroxyl group-containing betaine compound and long-chain alkyl group-containing betaine compound according to the present invention are highly biodegradable and useful as, for example, surfactants, bactericides, antistatic agents, softening agents, rust inhibitors, resin modifiers and synthetic intermediates.

By the processes for producing betaine compounds according to the present invention, hydroxyl group-containing betaine compounds and long-chain alkyl group-containing betaine compounds can be produced with high efficiency and in good yield.

BEST MODES FOR CARRYING OUT THE INVENTION

The following examples illustrate the present invention in further detail but are not intended to define the scope of the invention.

REFERENCE EXAMPLE 1

Synthesis of N,N-di-n-Butyl-β-alanine

A 300 ml four-necked flask equipped with a stirrer, condenser, thermometer and drip funnel was charged with 100 g (0.7738 mol) of di-n-butylamine and while the internal temperature was maintained at ≦30° C. on an iced-water bath, a mixture of 55.7 g (0.7730 mol) of acrylic acid and 0.1 g of phenothiazine was added dropwise over 30 minutes. After completion of dropwise addition, the reaction was carried out under heating on an oil bath at 80° C. for 4 hours.

After completion of the reaction, acrylic acid and di-n-butylamine were assayed by gas chromatography. As a result, formation of 152.5 g (yield 98%) of N,N-di-n-butyl-β-alanine was confirmed, with the rates of conversion of acrylic acid and di-n-butylamine being 98% and 98%, respectively.

REFERENCE EXAMPLE 2

Synthesis of N,N-di-n-Pentyl-β-alanine

A 100 ml four-necked flask equipped with a stirrer, condenser, thermometer and drip funnel was charged with 50 g (0.3179 mol) of di-n-pentylamine and while the internal temperature was maintained at ≦30° C. on an iced-water bath, a mixture of 22.9 g (0.3178 mol) of acrylic acid and 0.05 g of phenothiazine was added dropwise over 30 minutes. After completion of dropwise addition, the reaction was carried out under heating on an oil bath at 80° C. for 4 hours.

After completion of the reaction, acrylic acid and di-n-pentylamine were assayed by gas chromatography. As a result, formation of 69.2 g (yield 95%) of N,N-di-n-pentyl-β-alanine was confirmed, with the rates of conversion of acrylic acid and di-n-pentylamine being 95% and 95%, respectively.

REFERENCE EXAMPLE 3

Synthesis of N,N-di-(2-Hydroxy)ethyl-β-alanine

A 100 ml four-necked flask equipped with a stirrer, condenser, thermometer and drip funnel was charged with 50 g (0.4756 mol) of di (2-hydroxy) ethylamine and while the internal temperature was maintained at ≦30° C. on an iced-water bath with stirring, a mixture of 34.2 g (0.4751 mol) of acrylic acid and 0.02 g of phenothiazine was added dropwise over 1 hour. After completion of dropwise addition, the reaction was carried out under heating on an oil bath at 80° C. for 3 hours.

After completion of the reaction, acrylic acid and di(2-hydroxy)ethylamine were assayed by gas chromatography. As a result, formation of 83.3 g (yield 99%) of N,N-di(2-hydroxy)ethyl-β-alanine was confirmed, with the rates of conversion of acrylic acid and di(2-hydroxy)ethylamine being 99% and 99%, respectively.

EXAMPLE 1

Synthesis of 3-(N.N-di-n-Butyl-N-(2-hydroxy)propyl)ammoniopropanoate [a Hydroxy-containing Betaine compound 1]

A 100 ml laboratory-scale autoclave equipped with a stirrer and thermometer was charged with 30 g (0.1490 moi) of the N,N-di-n-butyl-β-alanine obtained in Reference Example 1, 8.66 g (0.1491 mol) of propylene oxide as the monooxirane, and 20 g of isopropyl alcohol and 1 g of water, both as the solvent. After 3 cycles of nitrogen purging at room temperature, nitrogen gas was introduced into the autoclave to establish an internal pressure of 3 atm. Then, the reaction was carried out under heating on an oil bath at 80° C. with constant stirring for 8 hours. The internal pressure was 3.6 atm in an initial phase of the reaction but dropped to 3.4 atm in 6 hours.

After the reaction mixture was cooled to room temperature, the nitrogen gas was driven out and the reaction mixture was transferred to a 500 ml eggplant-shaped flask. Using a rotary evaporator, the isopropyl alcohol and water were distilled off to recover about 38.5 g (yield 99.5%) of a hydroxyl group-containing betaine compound of the present invention, namely 3-(N,N-di-n-butyl-N-(2-hydroxy)propyl)ammoniopropanoate [hydroxy-containing betaine compound 1].

Figure 2:
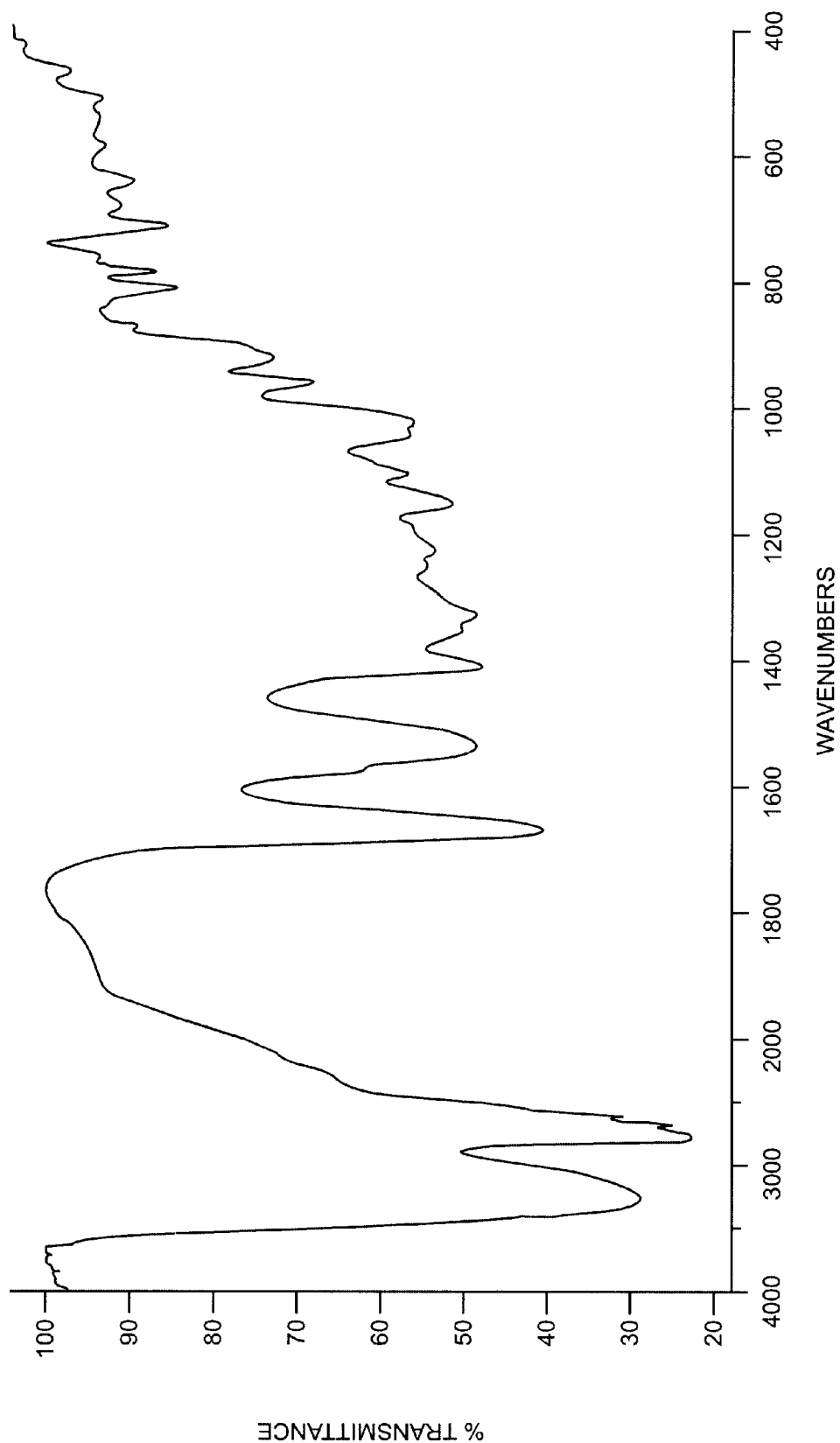
FIG. 2 is an infrared absorption spectrum of the hydroxyl group-containing betaine compound 1 obtained in Example 1.

The ¹H-nuclear magnetic resonance spectrum and infrared absorption spectrum of the obtained hydroxy-containing betaine compound 1 are shown in FIG. 1 and FIG. 2, respectively.

FIG. 1 shows a peak assignable to the methine group derived from propylene oxide at 4.0 ppm, which represents a chemical shift of about 1.0 ppm from the methine peak (3.0 ppm) of unreacted propylene oxide. On the other hand, FIG. 2 reveals the disappearance of the absorption (2550 to 2600 cm⁻¹) of the amino group of N,N-di-n-butyl-β-alanine. Observed, instead, are the absorptions of —CH₂—N⁺ and —CH—OH formed de novo around 840 cm⁻¹, 950 cm⁻¹, 1140 cm⁻¹ and 1200 cm⁻¹, as well as OH-stretching vibrations at 3300 to 3400 cm⁻¹.

The above data indicate the formation of a hydroxy-containing betaine compound 1 of the following formula (7).

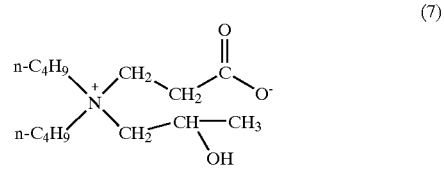

(7)

EXAMPLE 2

Synthesis of 3-(N,N-di-n-butyl-N-(2-hydroxy)ethyl)ammoniopropanoate [hydroxy-containing Betaine Compound 2]

A 100 ml laboratory-scale autoclave equipped with a stirrer and thermometer was charged with 30 g (0.1490 mol) of the N,N-di-n-butyl-β-alanine obtained in Reference Example 1 and 25 g of 1,2-dimethoxyethane plus 2 g of water, both as the solvent. After 3 cycles of nitrogen purging at room temperature, nitrogen gas was introduced into the autoclave to establish an internal pressure of 5 atm. The autoclave was then heated to a constant internal temperature on an oil bath at 80° C. When the internal temperature had steadied, 7.5 g (0.1703 mol) of ethylene oxide as the monooxirane compound was serially added over 10 minutes, exercising care not to allow the internal pressure of the autoclave to exceed 8 atm. After completion of addition, the reaction was conducted under heating on an oil bath at 80° C. with constant stirring for 6 hours. The internal pressure was 8 atm immediately after addition of ethylene oxide but dropped to 5.1 atm in 6 hours.

After the resulting reaction mixture was cooled to room temperature, the nitrogen gas and the residual ethylene oxide were driven out and the reaction mixture was transferred to a 500 ml eggplant-shaped flask. Using a rotary evaporator, the 1,2-dimethoxyethane and water were distilled off to recover about 36.2 g (yield 99%) of a hydroxyl group-containing betaine compound according to the present invention, namely 3-(N,N-di-n-butyl-N-(2-hydroxy)ethyl)ammoniopropanoate [hydroxy-containing betaine compound 2].

Figure 3:
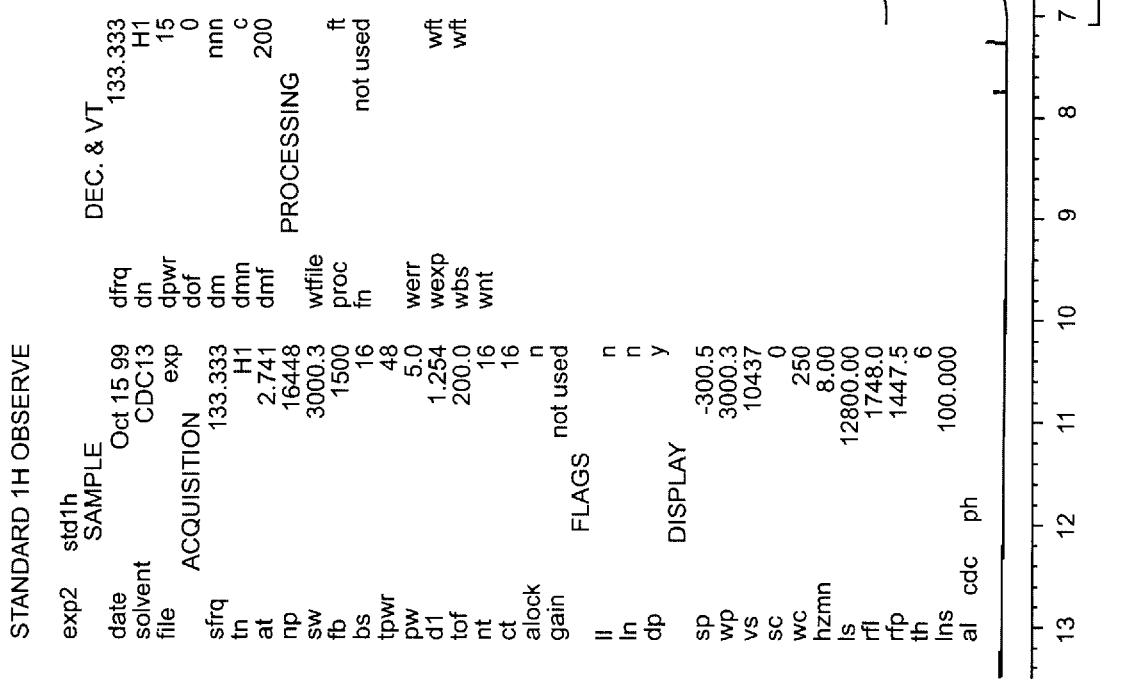
FIG. 3 is a $^1$H-nuclear magnetic resonance spectrum of the hydroxyl group-containing betaine compound 2 obtained in Example 2.
Figure 4:
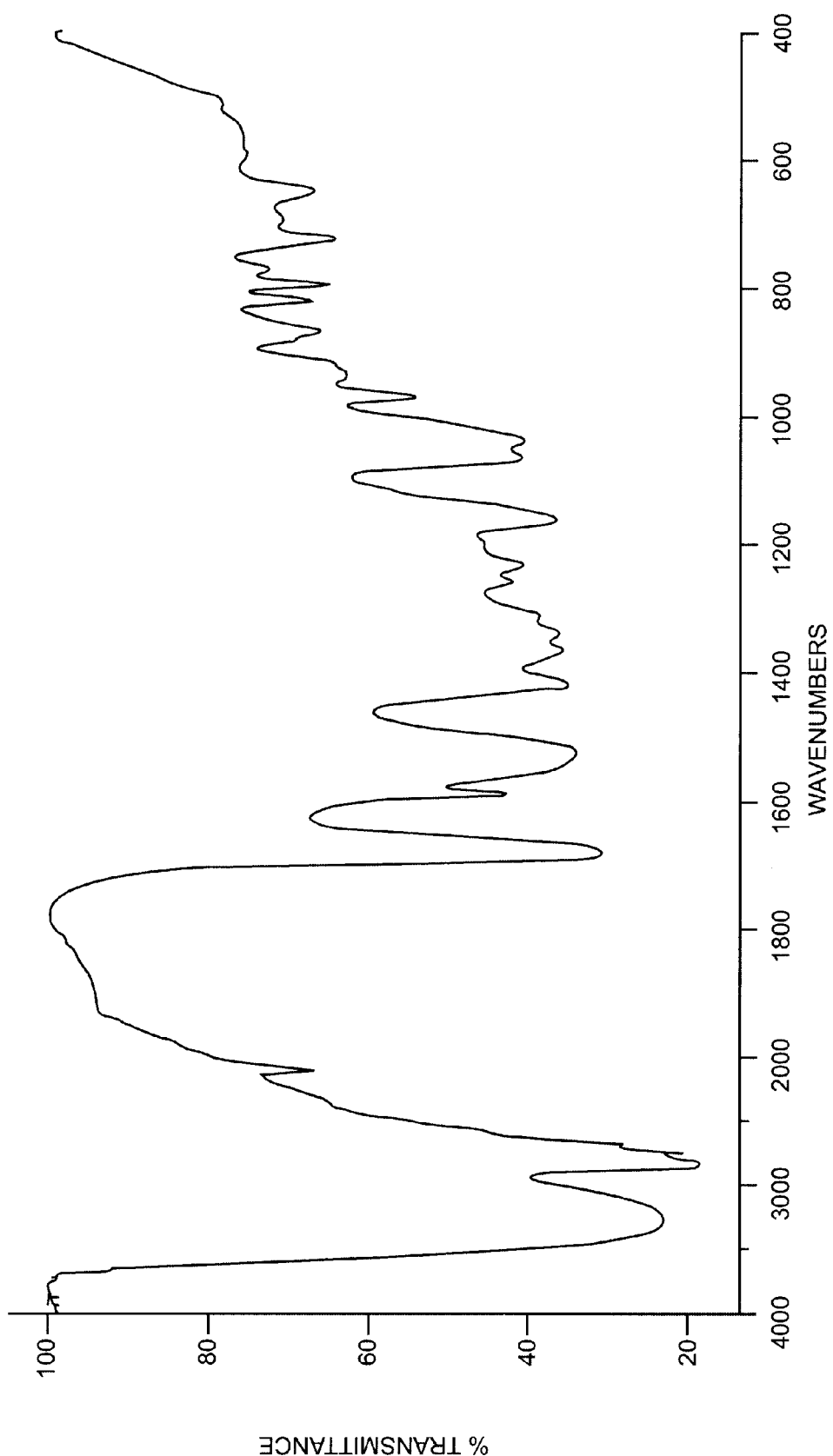
FIG. 4 is an infrared absorption spectrum of the hydroxyl group-containing betaine compound 2 obtained in Example 2.

The ¹H-nuclear magnetic resonance spectrum and infrared absorption spectrum of the obtained hydroxy-containing betaine compound 2 are shown in FIG. 3 and FIG. 4, respectively.

FIG. 3 shows a proton peak assignable to the methylene group derived from ethylene oxide at 4.2 ppm, which represents a shift of about 1.7 ppm from the peak (2.5 ppm) of the methylene group of unreacted ethylene oxide. FIG. 4 shows the disappearance of the absorption (2550 to 2600 cm$^{-1}$) of an amino group in the starting material N,N-di-n-butyl-β-alanine. Observed, instead, are the absorptions of —CH$_2$—N$^+$ and —CH—OH formed de novo around 830 cm$^{-1}$, 950 cm$^{-1}$ and 1200 cm$^{-1}$, and OH-stretching vibrations at 3200 to 3400 cm$^{-1}$.

The above data indicate the formation of a hydroxy-containing betaine compound 2 of the following formula (8).

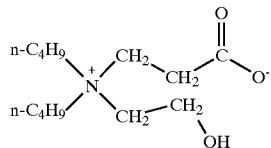

(8)

EXAMPLE 3

Synthesis of 3-(N,N-di-n-Pentyl-N-(2-hydroxy)propyl)ammoniopropanoate [Hydroxy-containing Betaine Compound 3]

A 100 ml laboratory-scale autoclave equipped with a stirrer and thermometer was charged with 25 g (0.1090 mol) of the N,N-di-n-pentyl-β-alanine obtained in Reference Example 2, 7 g (0.1205 mol) of propylene oxide as the monooxirane, and 20 g of 1,2-dimethoxyethane and 2 g of water, both as the solvent. After 3 cycles of nitrogen purging at room temperature, nitrogen gas was introduced into the autoclave to establish an internal pressure of 3 atm. Then, the reaction was carried out on an oil bath at 80° C. with constant stirring for 8 hours. The internal pressure was 4.1 atm in an initial phase of the reaction but dropped to 3.4 atm in 6 hours.

After the reactionmixture was cooled to room temperature, the nitrogen gas was driven out and the reaction mixture was transferred to a 500 ml eggplant-shaped flask. Using a rotary evaporator, the 1,2-dimethoxyethane and water were distilled off to recover about 31 g (yield 99%) of a hydroxyl group-containing betaine compound of the present invention, namely 3-(N,N-di-n-pentyl-N-(2-hydroxy)propyl)ammoniopropanoate [hydroxy-containing betaine compound 3].

Figure 5:
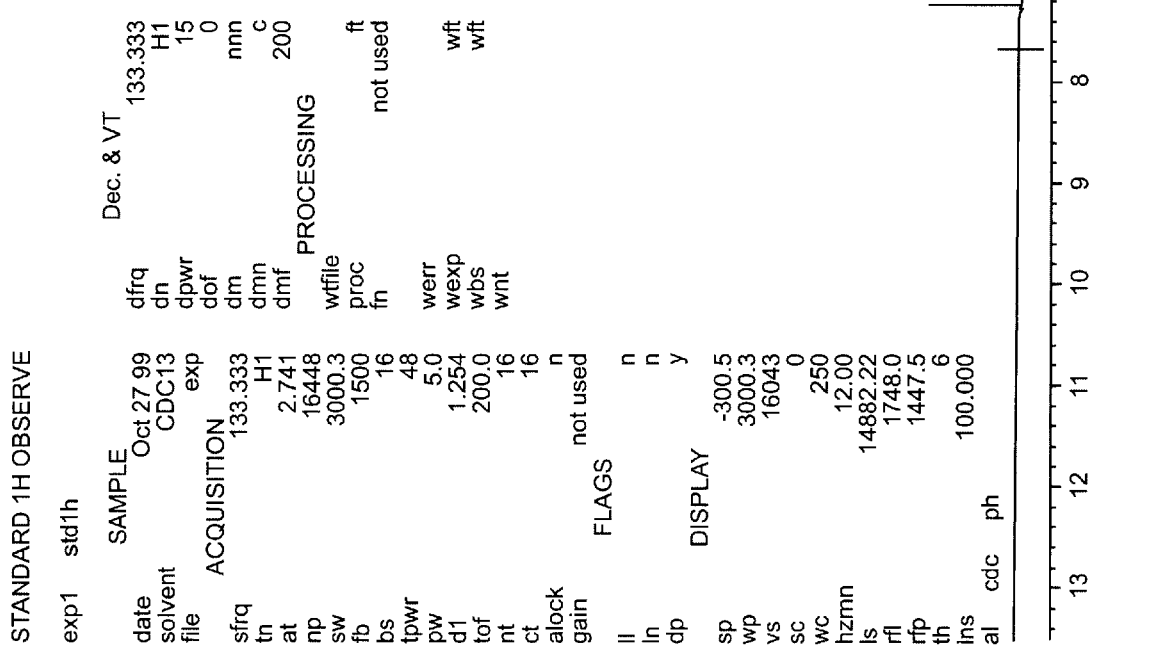
FIG. 5 is a $^1$H-nuclear magnetic resonance spectrum of the hydroxyl group-containing betaine compound 3 obtained in Example 3.
Figure 6:
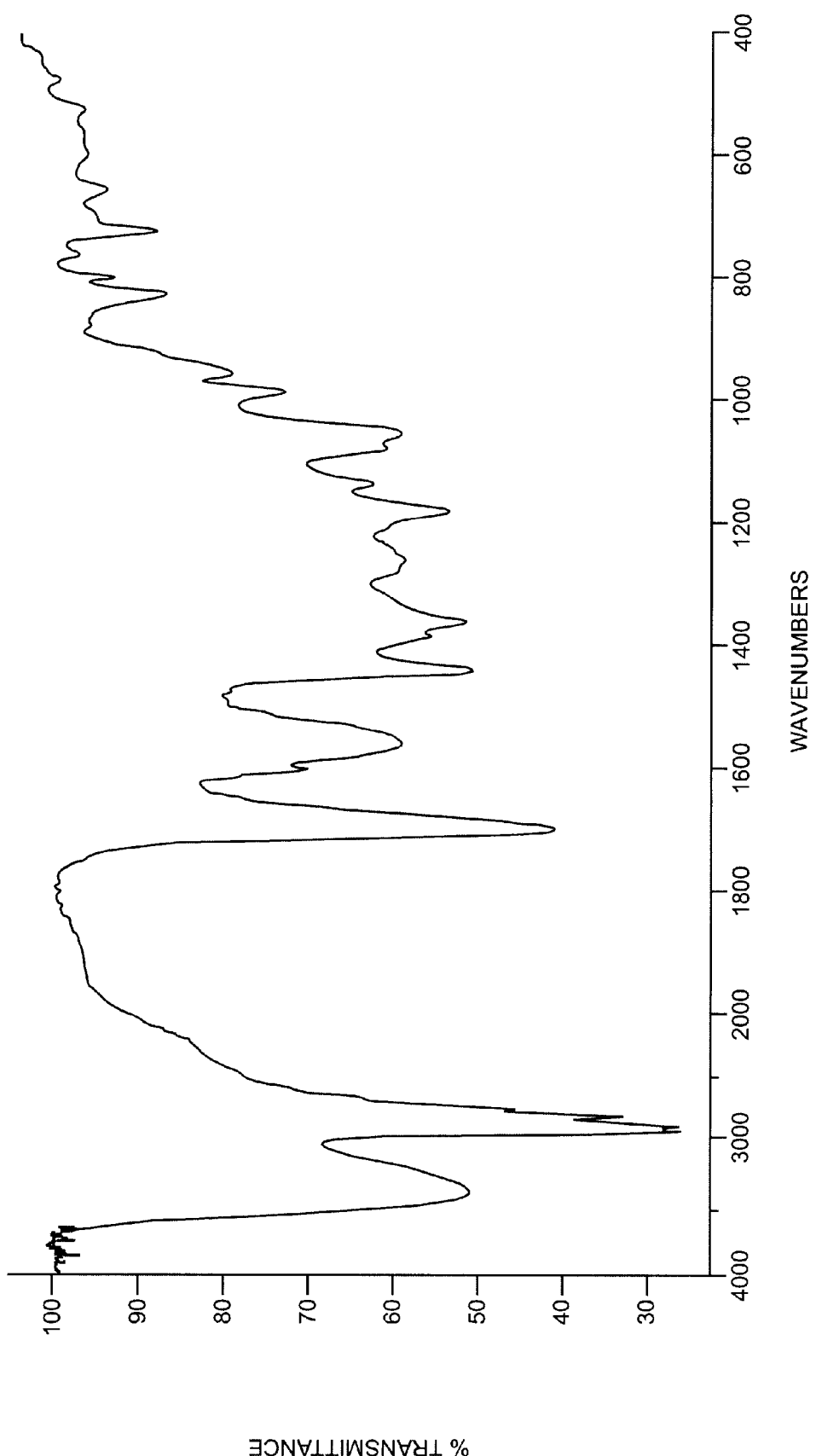
FIG. 6 is an infrared absorption spectrum of the hydroxyl group-containing betaine compound 3 obtained in Example 3.

The $^1$H-nuclear magnetic resonance spectrum and infrared absorption spectrum of the obtained hydroxy-containing betaine compound 3 are shown in FIG. 5 and FIG. 6, respectively.

FIG. 5 shows a peak assignable to the methine group derived from propylene oxide at 4.0 ppm, which represents a chemical shift of about 1.0 ppm from the methine peak (3.0 ppm) of unreacted propylene oxide. FIG. 6 shows the disappearance of the absorption (2550 to 2600 cm$^{-1}$) of the amino group of N,N-di-n-pentyl-β-alanine. Observed, instead, are the absorptions of —CH$_2$—N$^+$ and —CH—OH formed de novo around 840 cm$^{-1}$, 960 cm$^{-1}$, 1150 cm$^{-1}$ and 1200 cm$^{-1}$, as well as OH-stretching vibrations at 3300 to 3400 cm$^{-1}$.

The above data indicate the formation of the hydroxy-containing betaine compound 3 of the following formula (9).

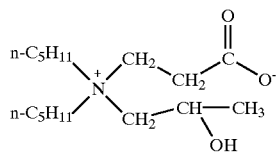

(9)

EXAMPLE 4

Synthesis of 3-(N,N-di-n-Butyl-N-(2-(3-carboxyl-3-dodecenyl-1-oxo)propoxy)propyl)ammoniopropanoate [a Long-Chain Alkyl Grourp-containing Betaine Compound 1]

A 100 ml four-necked flask equipped with a stirrer, condenser, thermometer and drip funnel was charged with 20 g (0.0771 mmol) of the 3-(N,N-di-n-butyl-N-(2-hydroxy)propyl)ammoniopropanoate [hydroxy-containingbetaine compound 1] obtained in Example 1 and 30 g of toluene as the solvent and while the mixture was heated on an oil bath at 80° C. with constant stirring, 20.54 g (0.0771 mol) of dodecenylsuccinic anhydride was added dropwise over 5 minutes. After completion of dropwise addition, the reaction was conducted under heating on an oil bath at 80° C. for 3 hours.

After completion of the reaction, the reaction mixture was transferred to a 500 ml eggplant-shaped flask. Using a rotary evaporator, toluene was distilled off to recover about 40.5 g (yield 99.9%) of a long-chain alkyl group-containing betaine compound according to the present invention, namely 3-(N,N-di-n-butyl-N-(2-(3-carboxyl-3-dodecenyl-1-oxo)propoxy)propyl)ammoniopropanoate [a long-chain alkyl group-containing betaine compound 1].

Figure 7:
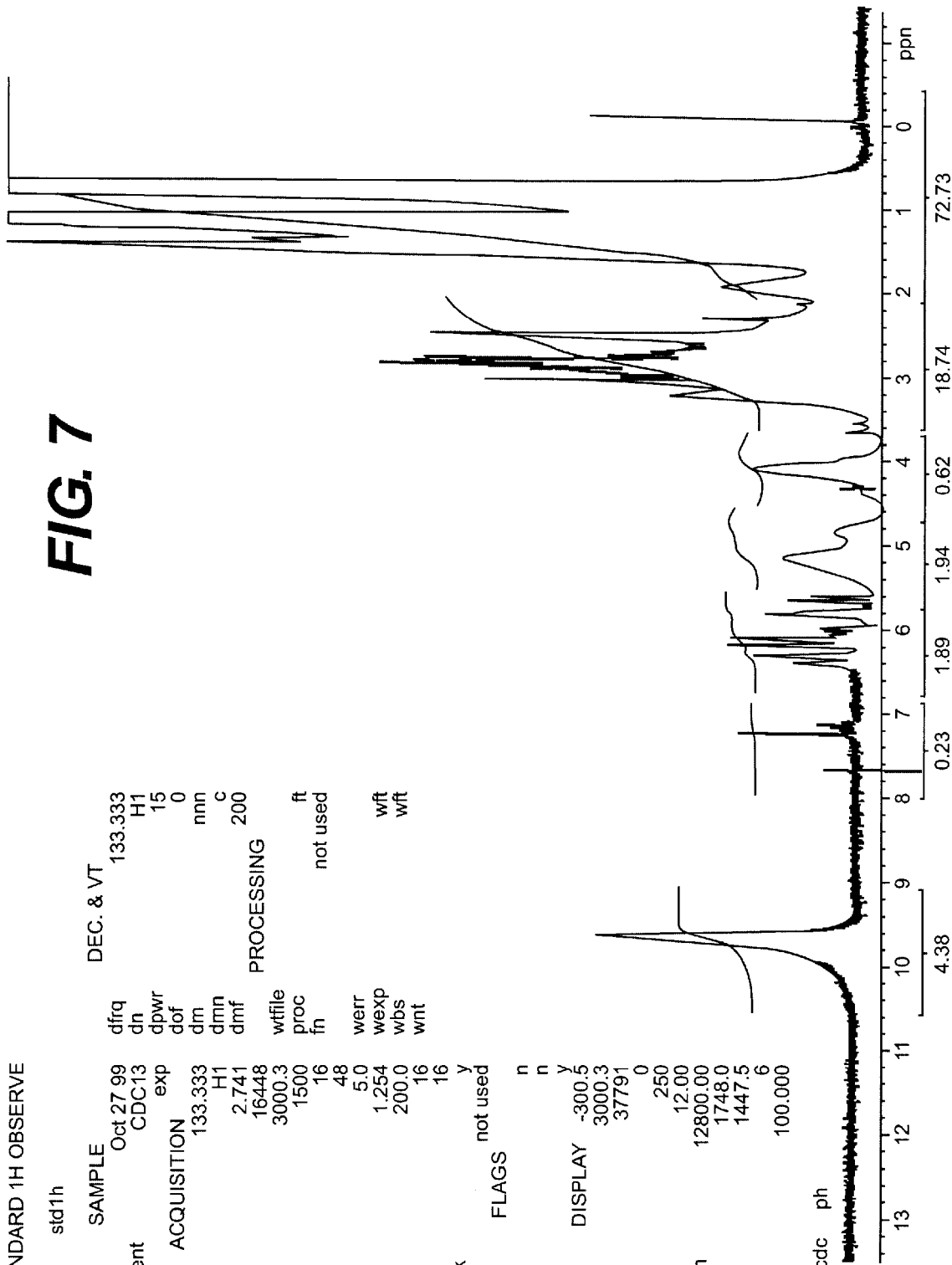
FIG. 7 is a $^1$H-nuclear magnetic resonance spectrum of the long-chain alkyl group-containing betaine compound 1 obtained in Example 4.
Figure 8:
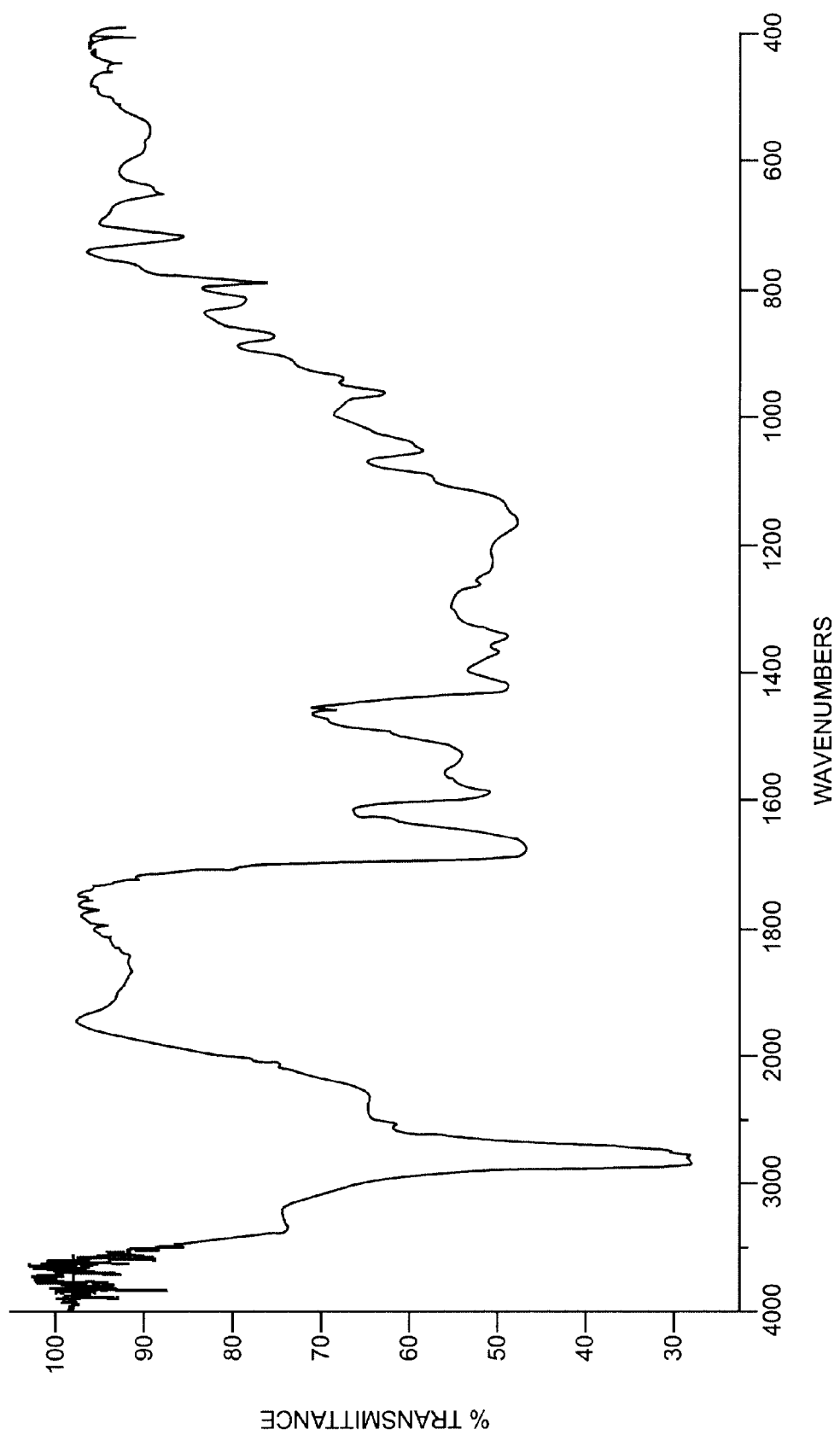
FIG. 8 is an infrared absorption spectrum of the long-chain alkyl group-containing betaine compound 1 obtained in Example 4.

The $^1$H-nuclear magnetic resonance spectrum and infrared absorption spectrum of the long-chain alkyl group-containing betaine compound 1 are shown in FIG. 7 and FIG. 8, respectively.

FIG. 7 shows a peak assignable to the methine group derived from propylene oxide at 4.1 to 4.2 ppm, which represents a chemical shift of about 0.1 ppm from the methine peak (4.0 ppm) of unreacted propylene oxide. In addition, a peak assignable to a proton in the carboxyl group formed on ring-opening of the dodecenylsuccinic anhydride was found at 9.6 to 9.8 ppm. FIG. 8 shows the disappearance of the OH— stretching vibrations at 3300 to 3400 cm$^{-1}$ and, instead, the appearance of CO$_2$—H stretching vibrations of the carboxyl group formed on ring-opening of the dodecenylsuccinic acid at 2500 to 2600 cm$^{-1}$.

The above data indicate the formation of a long-chain alkyl group-containing betaine compound 1 of the following formula (10).

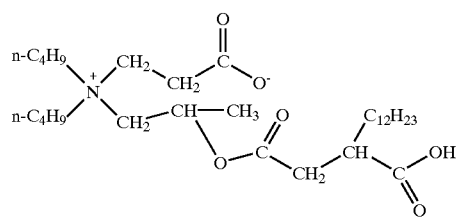

(10)

EXAMPLE 5

Synthesis of 3-(N,N-di-n-Butyl-N-(2-cococarboxy)propyl)ammoniopropanoate [Long-chain Alkyl Group-containing Betaine Compound 2]

A 100 ml four-necked flask equipped with a stirrer, condenser, thermometer and Dean-Stark trap was charged with 15 g (0.0578 mol) of the 3-(N,N-di-n-butyl-N-(2-hydroxy)propyl)aammoniopropanoate [hydroxy-containing betaine compound 1] obtained in Example 1, 13 g (0.0579 mol) of cocoalkyl-carboxylic acid, 20 g of toluene as the solvent, and 0.2 g of p-toluenesulfonic acid as the catalyst, and the reaction was conducted under heating on an oil bath at 140° C. with constant stirring for 18 hours.

By the end of the above reaction time, the amount of water removed was 0.98 g, while the theoretical amount of dehydration is 1.04 g. Therefore, the conversion rate of this dehydration reaction was 94%.

The above reaction mixture was transferred to a 500 ml eggplant-shaped flask and the toluene was distilled off using a rotary evaporator to recover about 25.2 g (yield 94%) of a long-chain alkyl group-containing betaine compound according to the present invention, namely 3-(N,N-di-n-butyl-N-(2-cococarboxy)propyl)ammoniopropanoate [long-chain alkyl group-containing betaine compound 2].

Figure 9:
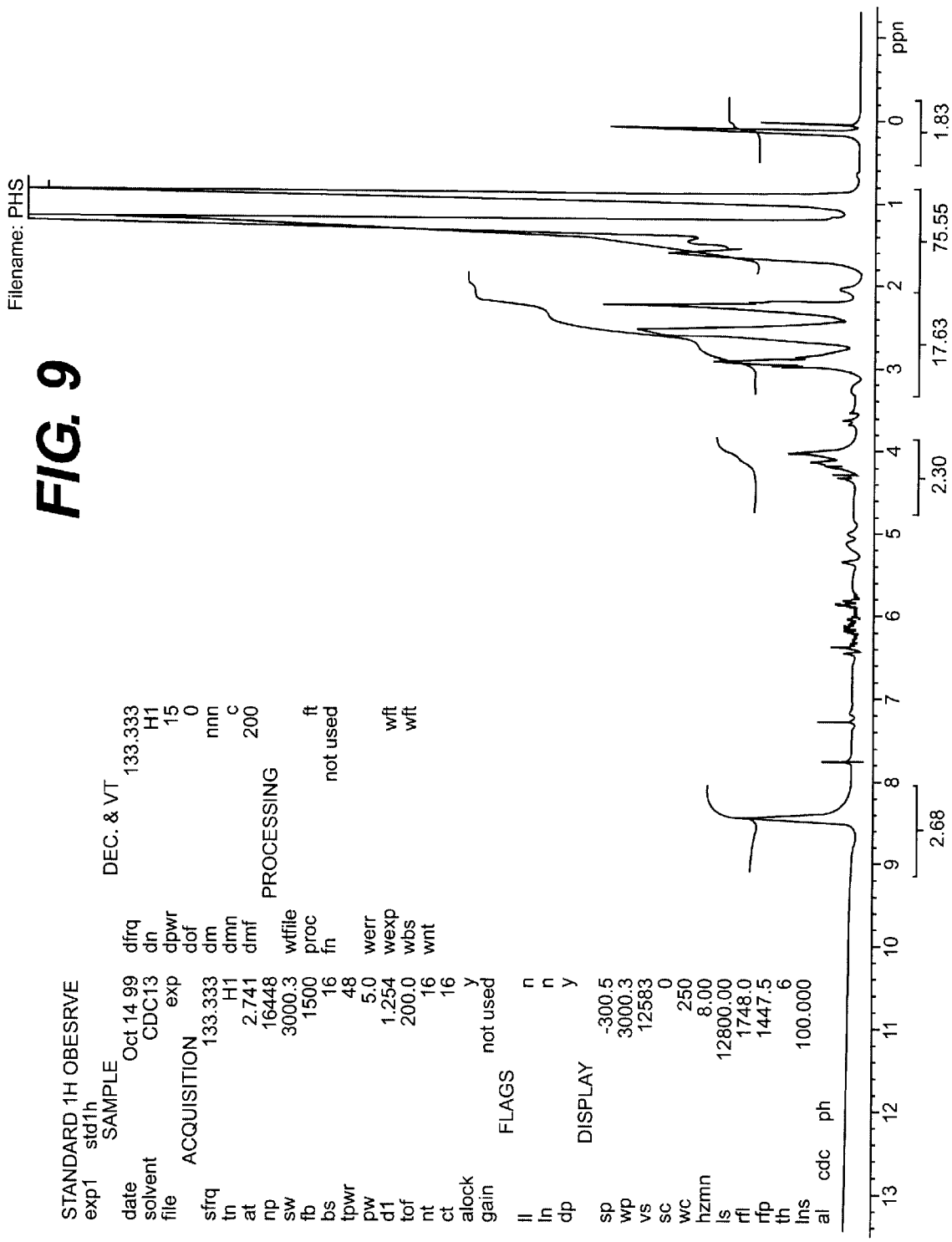
FIG. 9 is a $^1$H-nuclear magnetic resonance spectrum of the long-chain alkyl group-containing betaine compound 2 obtained in Example 5.
Figure 10:
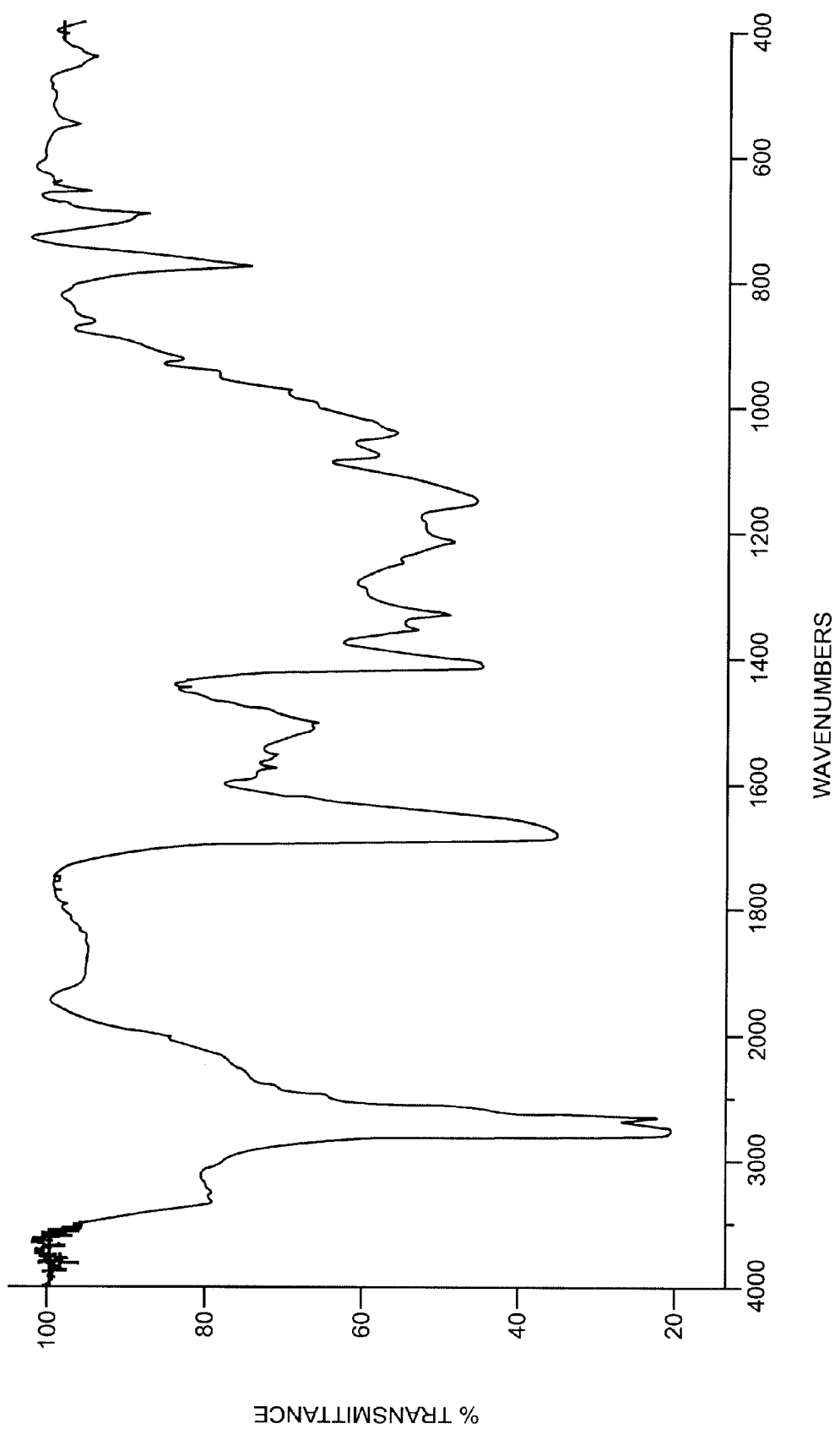
FIG. 10 is an infrared absorption spectrum of the long-chain alkyl group-containing betaine compound 2 obtained in Example 5.

The $^1$H-nuclear magnetic resonance spectrum and infrared absorption spectrum of this long-chain alkyl group-containing betaine compound 1 are shown in FIG. 9 and FIG. 10, respectively.

FIG. 9 shows a peak assignable to the methine group deived from propyene oxide at 4.1 to4.2 ppm, which represents a chemical shift of about 1.0 ppm from the methine peak (4.0 ppm) of unreacted propylene oxide. FIG. 10 shows not only the disappearance of the OH-stretching vibrations at 3300 to 3400 cm$^{-1}$ but also the disappearance of $CO_2$—H stretching vibrations due to the carboxyl group of unreacted cocoalkyl-carboxylic acid around 2550 to 2600 cm$^{-1}$.

The above data indicate the formation of a long-chain alkyl group-containing betaine compound 2 of the following formula (11):

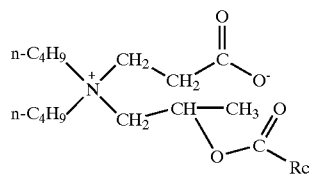

(11)

wherein Rc represents cocoalkyl.

EXAMPLE 6

Synthesis of 3-(N,N-di-n-Butyl-N-(2-(3-carboxyl-3-dodecenyl-1-oxo)propoxy)ethyl)ammoniopropanoate [Long-chain Alkyl Group-containing Betaine Compound 3]

A 100 ml four-necked flask equipped with a stirrer, condenser, thermometer and drip funnel was charged with 20 g (0.0815 mol) of the 3-(N,N-di-n-butyl-N-(2-hydroxy)ethyl)ammoniopropanoate [hydroxy-containing betaine compound 2] obtained in Example 2 and 30 g of toluene as the solvent and while the mixture was heated on an oil bath at 80° C. with stirring, 21.7 g (0.0815 mol) of dodecenyl-succinic anhydride was added dropwise over 5 minutes. After completion of dropwise addition, the reactionwas carriedout under heating on an oil bath at 80° C. for 3 hours.

After completion of the reaction, the reaction mixture was transferred to a 500 ml eggplant-shaped flask, and using a rotary evaporator the toluene was distilled off to recover 41.5 g (yield 99.5%) of 3-(N,N-di-n-butyl-N-(2-(3-carboxyl-3-dodecenyl-1-oxo)propoxy)ethyl) ammoniopropanoate [long-chain alkyl group-containing betaine compound 3].

Figure 11:
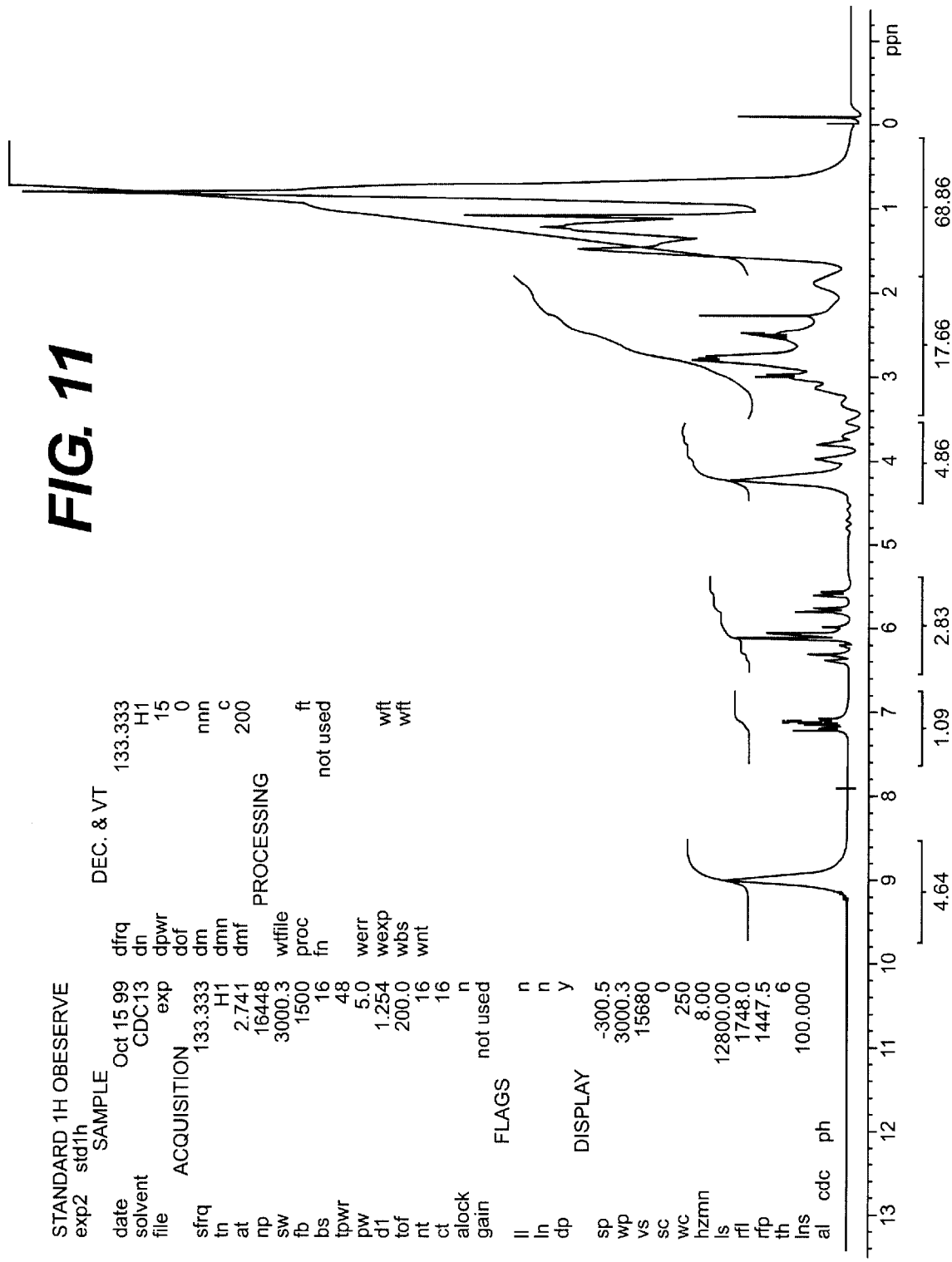
FIG. 11 is a $^1$H-nuclear magnetic resonance spectrum of the long-chain alkyl group-containing betaine compound 3 obtained in Example 6.
Figure 12:
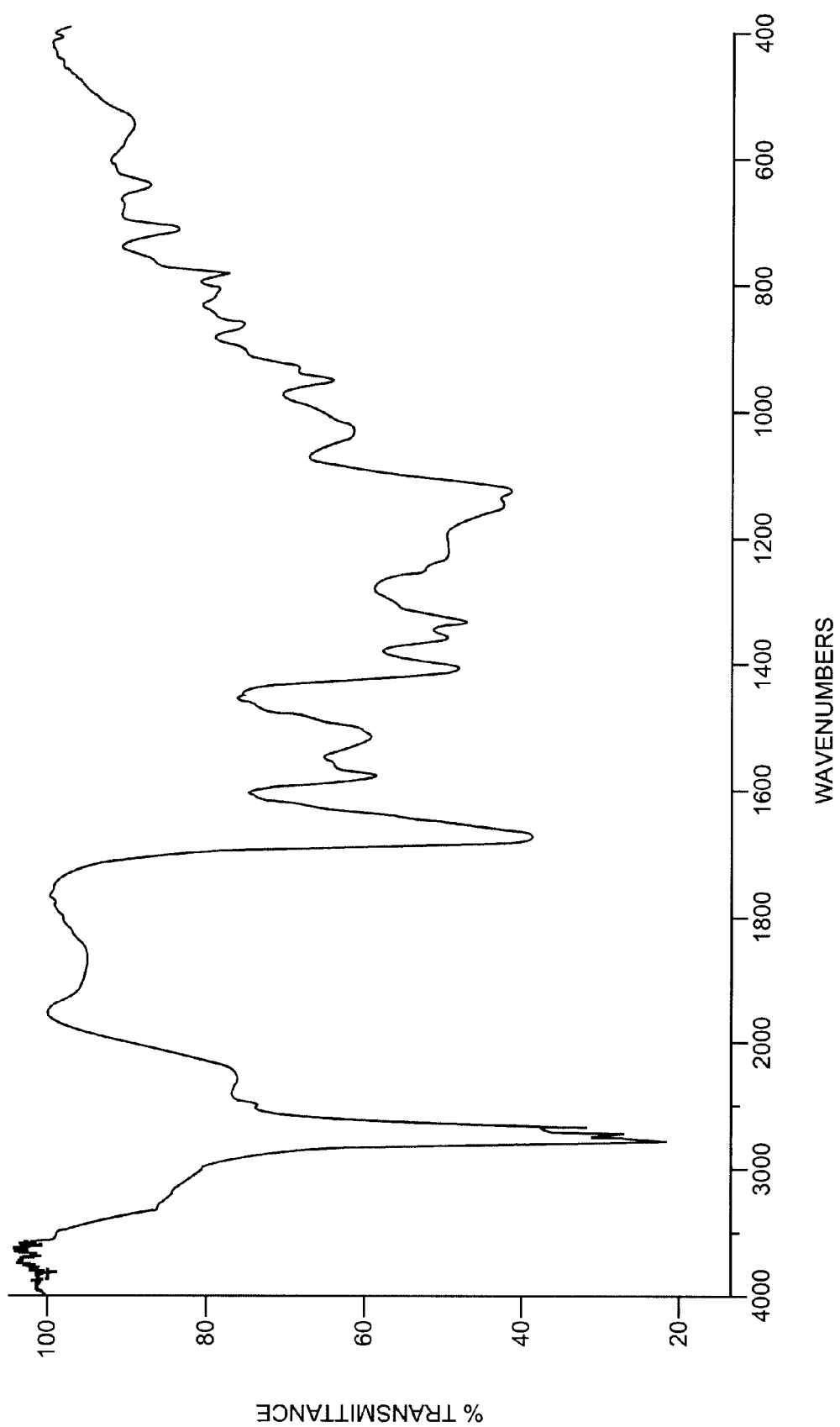
FIG. 12 is an infrared absorption spectrum of the long-chain alkyl group-containing betaine compound 3 obtained in Example 6.

The $^1$H-nuclear magnetic resonance spectrum and infrared absorption spectrum of the obtained long-chain alkyl group-containing betaine compound 3 are shown in FIG. 11 and FIG. 12, respectively.

FIG. 11 shows a peak assignable to the methylene group derived from ethylene oxide at 4.3 to 4.4 ppm, which represents a shift of about 0.1 ppm from the peak (around 4.2 ppm) of unreacted ethylene oxide. In addition, a peak assignable to a proton in the carboxyl group formed on ring-opening of the dodecenylsuccinic anhydride was found around 9.1 ppm. FIG. 12 shows the disappearance of the OH-stretching vibrations around 3300 to 3400 cm$^{-1}$ and, instead, the appearance of $CO_2$—H-streching vibrations in the neighborhood of 2500 to 2600 cm$^{-1}$.

The above data indicate the formation of a long-chain alkyl group-containing betaine compound 3 of the following formula (12).

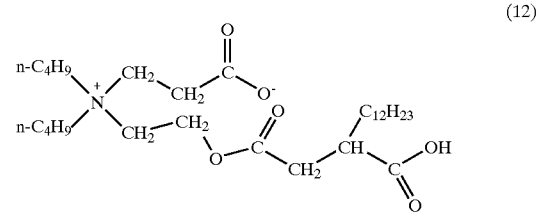

(12)

EXAMPLE 7

Synthesis of 3-(N.N-di-n-Butyl-N-(2-cococarboxy) ethyl)ammoniopropanoate [Long-chain Alkyl Group-containing Betaine Compound 4]

A 100 ml four-necked flask equipped with a stirrer, condenser, thermometer and Dean-Stark trap was charged with 13.5 g (0.0551 mol) of the 3-(N,N-di-n-butyl-N-(2-hydroxy)ethyl)ammoniopropanoate [hydroxy-containing betaine compound 2] obtained in Example 2, 12.3 g (0.0550 mol) of cocoalkyl-carboxylic acid, 20 g of toluene as the solvent, and 0.2 g of p-toluenesulfonic acid as the catalyst, and the reaction was conducted under heating on an oil bath at 140° C. with constant stirring for 19 hours.

By the end of the above reaction time, the amount of water removed was 0.95 g, while the theoretical amount of dehydration is 0.99 g. Therefore, the conversion rate of this dehydration reaction was found to be 96%.

The reaction mixture obtained above was transferred to a 500 ml eggplant-shaped flask, and using a rotary evaporator the toluene was distilled off to recover about 24.8 g (yield 96%) of a long-chain alkyl group-containing betaine compound according to the present invention, namely 3-(N,N-di-n-butyl-N-(2-cococarboxy)ethyl)ammoniopropanoate [long-chain alkyl group-containing betaine compound 4].

Figure 13:
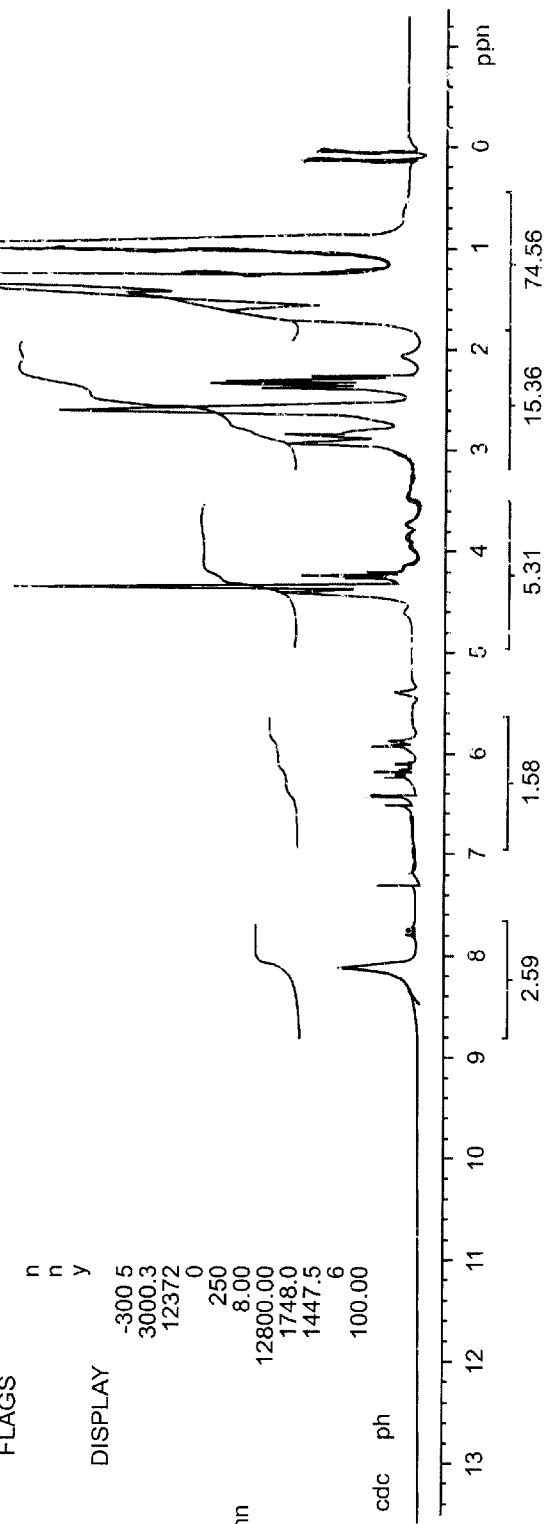
FIG. 13 is a $^1$H-nuclear magnetic resonance spectrum of the long-chain alkyl group-containing betaine compound 4 obtained in Example 7.
Figure 14:
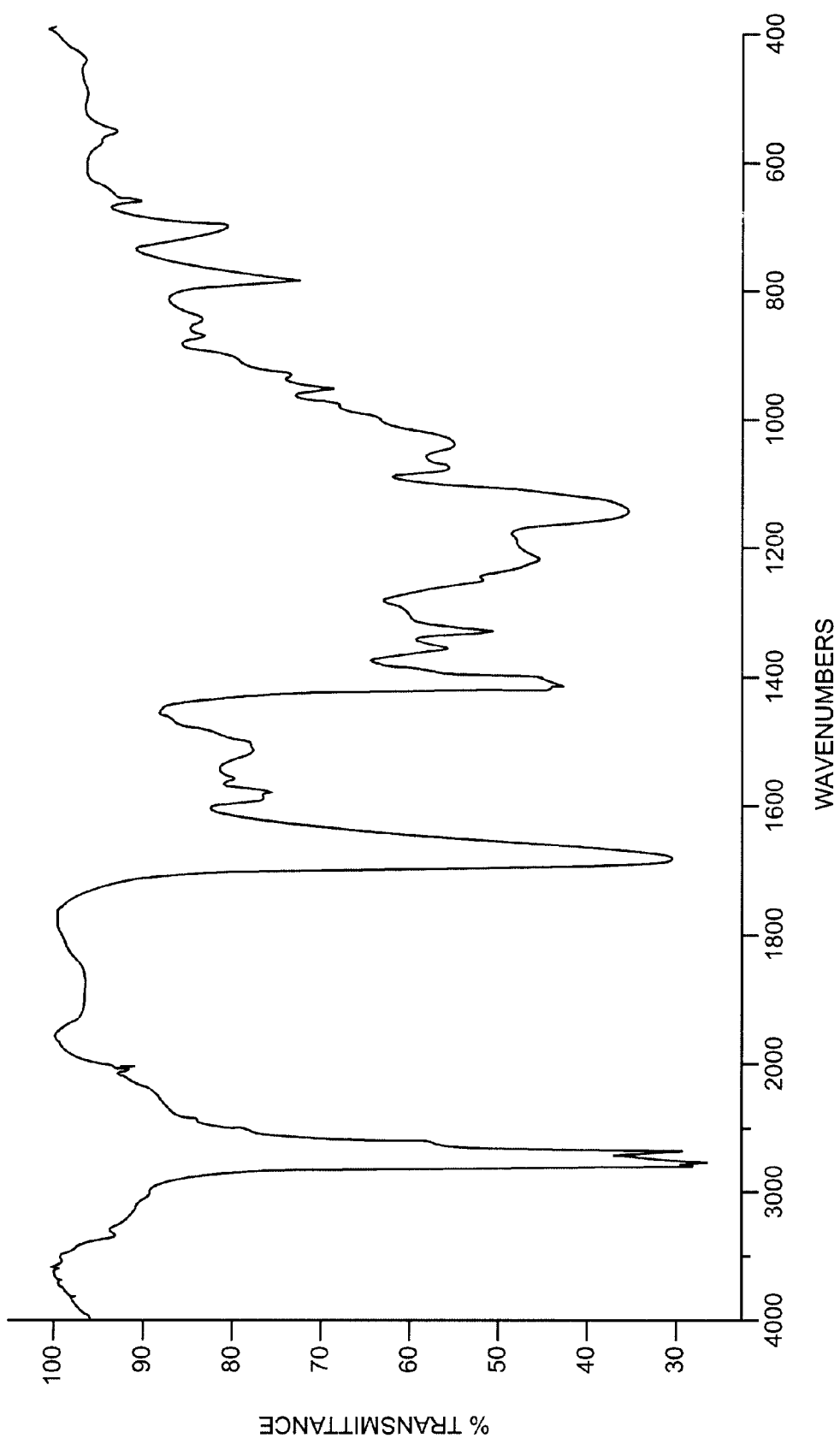
FIG. 14 is an infrared absorption spectrum of the long-chain alkyl group-containing betaine compound 4 obtained in Example 7.

The $^1$H-nuclear magnetic resonance spectrum and infrared absorption spectrum of the obtained long-chain alkyl group-containing betaine compound 4 are shown in FIG. 13 and FIG. 14, respectively.

FIG. 13 indicates a peak assignable to the methylene group derived from ethylene oxide at 4.2 to 4.4 ppm, which represents a chemical shift of about 0.2 ppm from the peak (around 4.1 to 4.2 ppm) of unreacted ethylene oxide. FIG. 14 indicates not only the disappearance of the OH-stretching vibrations at 3300 to 3400 cm$^{-1}$ but also the disappearance of the CO$_2$—H stretching vibrations due to the carboxyl group of unreacted cocoalkyl-carboxylic acid around 2550 to 2600 cm$^{-1}$.

The above data indicate the formation of a long-chain alkyl group-containing betaine compound 4 of the following formula (13):

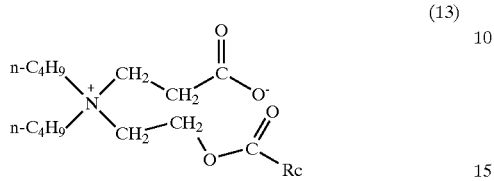
(13)

wherein Rc is as defined hereinbefore.

EXAMPLE 8

Synthesis of 3-(N,N-di-n-Pentyl-N-(2-(3-carboxy-3-dodecenyl-1-oxo)propoxy)propyl) ammoniopropanoate [Long-chain Alkyl Group-containing Betaine Compound 5]

A 100 ml four-necked flask equipped with a stirrer, condenser, thermometer and drip funnel was charged with 13 g (0.0452 mol) of the 3-(N,N-di-n-pentyl-N-(2-hydroxy) propyl)ammoniopropanoate [hydroxy-containing betaine compound 3] obtained in Example 3 and 30 g of toluene as the solvent and while the mixture was heated on an oil bath at 80° C. with constant stirring, 12 g (0.0451 mol) of dodecenylsuccinic anhydride was added dropwise over 5 minutes. After completion of dropwise addition, the reaction was carried out under heating on an oil bath at 80° C. for 3 hours.

After completion of the reaction, the reaction mixture was transferred to a 500 ml eggplant-shaped flask, and using a rotary evaporator the toluene was distilled off to recover 24.8 g (yield 99.2%) of 3-(N,N-di-n-pentyl-N-(2-(3-carboxyl-3-dodecenyl-1-oxo) propoxy) propyl) ammoniopropanoate [long-chain alkyl group-containing betaine compound 5].

Figure 15:
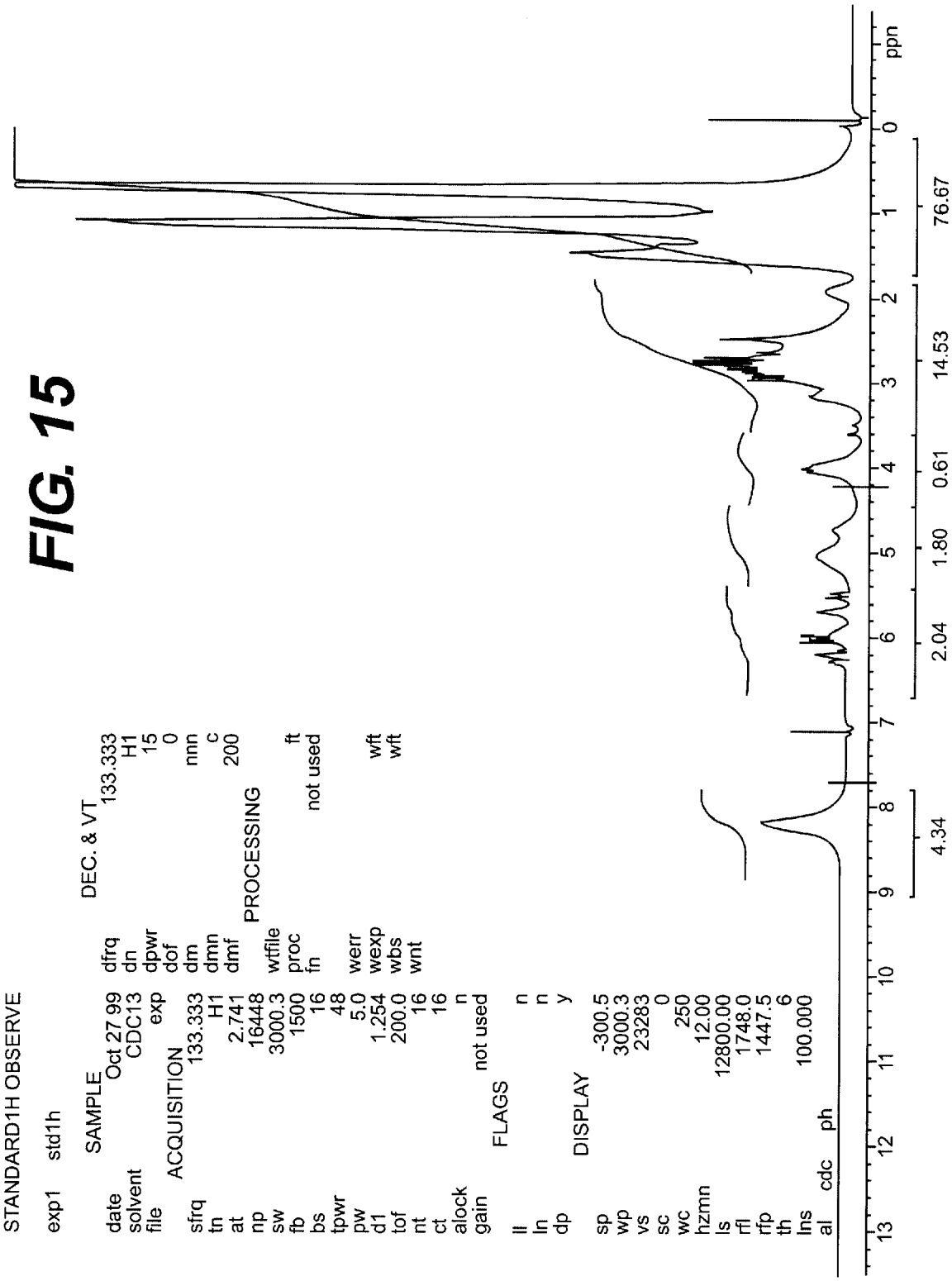
FIG. 15 is a $^1$H-nuclear magnetic resonance spectrum of the long-chain alkyl group-containing betaine compound 5 obtained in Example 8.
Figure 16:
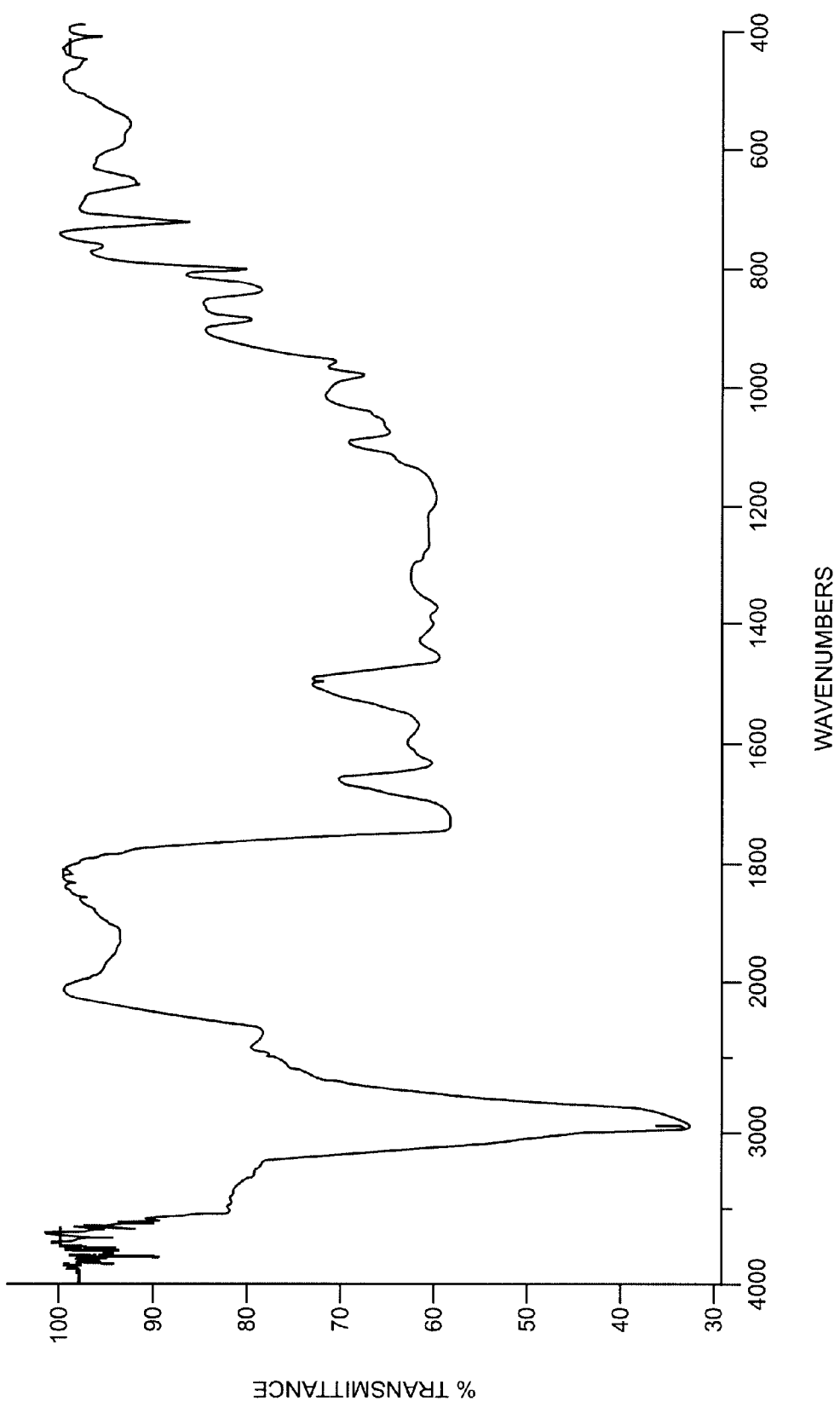
FIG. 16 is an infrared absorption spectrum of the long-chain alkyl group-containing betaine compound 5 obtained in Example 8.

The $^1$H-nuclear magnetic resonance spectrum and infrared absorption spectrum of the obtained long-chain alkyl group-containing betaine compound 5 are shown in FIG. 15 and FIG. 16, respectively.

FIG. 15 shows a peak assignable to the methine group derived from propylene oxide at 4.1 to 4.2 ppm, which represents a chemical shift of about 0.1 ppm from the peak (around 4.0 ppm) of unreacted propylene oxide. In addition, a peak assignable to a proton in the carboxyl group formed on ring-opening of the dodecenylsuccinic anhydride was found around 8.4 ppm. FIG. 16 shows the disappearance of the OH-stretching vibrations around 3300 cm$_{-1}$ and, instead, the appearance of CO$_2$—H-streching vibrations in the neighborhood of 2500 to 2550 cm$^{-1}$.

The above data indicate the formation of a long-chain alkyl group-containing betaine compound 5 of the following formula (14).

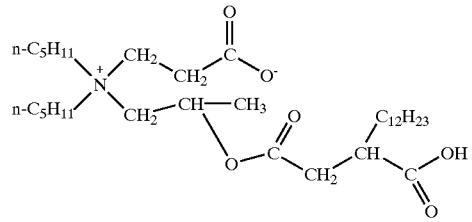
(14)

EXAMPLE 9

Synthesis of 3-(N.N-di-n-Pentyl-N-(2-cococarboxy) propyl)ammoniopropanoate [Long-chain Alkyl Group-containing Betaine Compound 6]

A 100 ml four-necked flask equipped with a stirrer, condenser, thermometer and Dean-Stark trap was charged with 13.5 g (0.0470 mol) of the 3-(N,N-di-n-pentyl-N-(2-hydroxy)propyl)ammoniopropanoate [hydroxy-containing betaine compound 3] obtained in Example 3, 10.5 g (0.0469 mol) of cocoalkyl-carboxylic acid, 20 g of toluene as the solvent, and 0.2 g of p-toluenesulfonic acid as the catalyst, and the reaction was conducted under heating on an oil bath at 140° C. with constant stirring for 16 hours.

By the end of the above reaction time, the amount of water removed was 0.81 g, while the theoretical amount of dehydration is 0.85 g. Therefore, the conversion rate of this dehydration reaction was found to be 95%.

The reaction mixture obtained above was transferred to a 500 ml eggplant-shaped flask, and using a rotary evaporator the toluene was distilled off to recover about 22 g (yield 95%) of a long-chain alkyl group-containing betaine compound 6 according to the present invention, namely 3-(N,N-di-n-pentyl-N-(2-cococarboxy)propyl) ammoniopropanoate [long-chain alkyl group-containing betaine compound 6].

Figure 17:
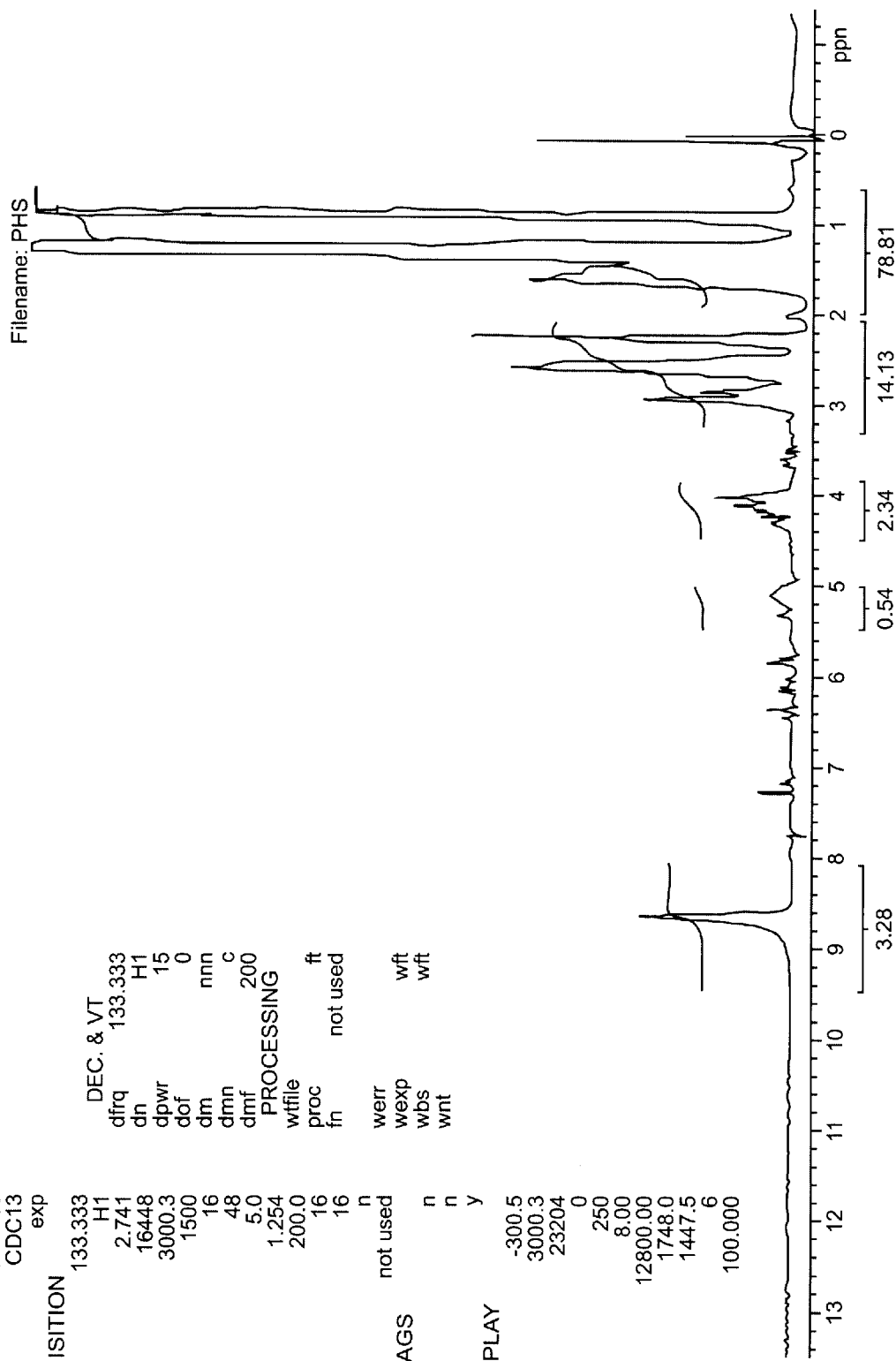
FIG. 17 is a $^1$H-nuclear magnetic resonance spectrum of the long-chain alkyl group-containing betaine compound 6 obtained in Example 9.
Figure 18:
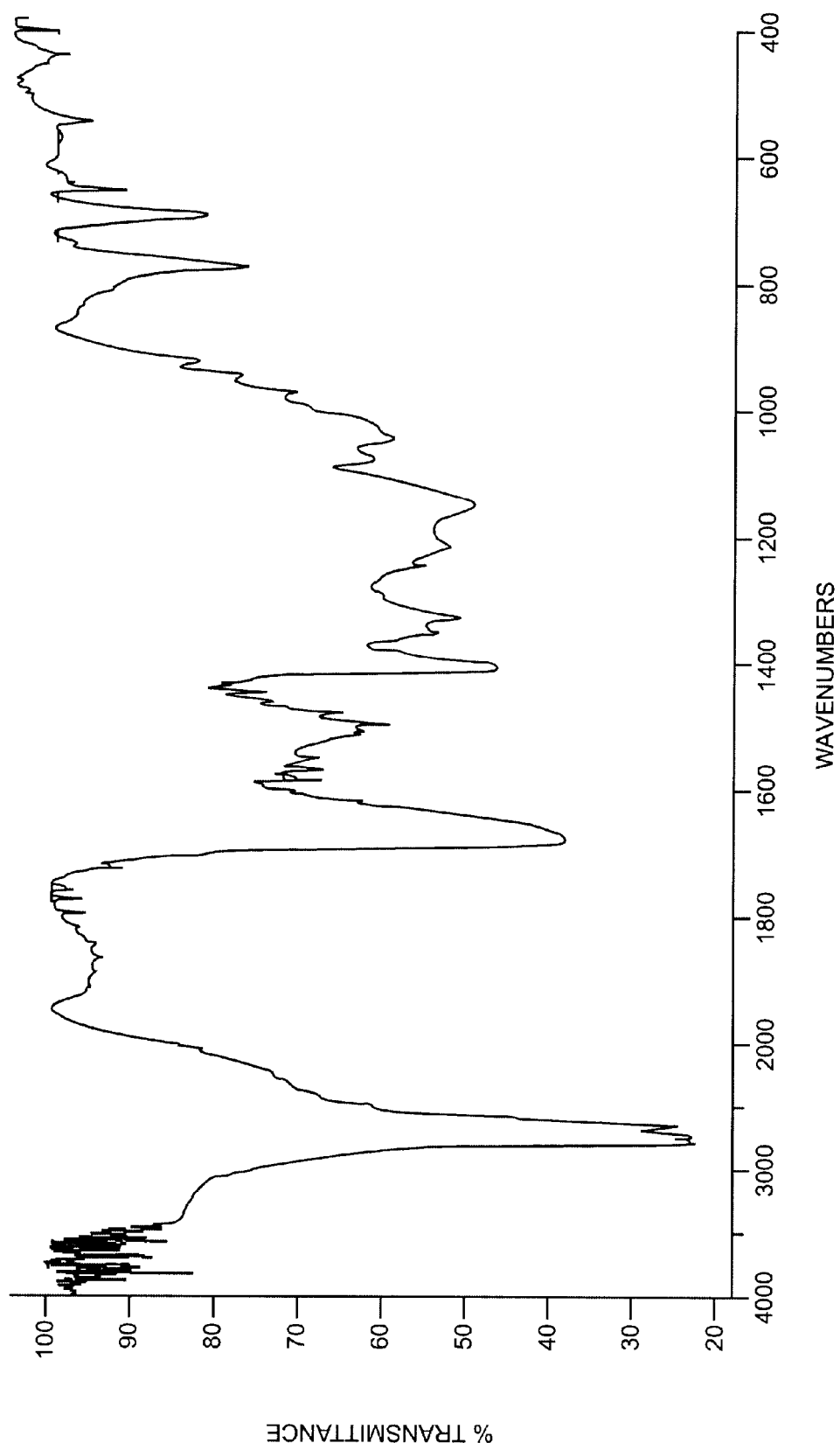
FIG. 18 is an infrared absorption spectrum of the long-chain alkyl group-containing betaine compound 6 obtained in Example 9.

The $^1$H-nuclear magnetic resonance spectrum and infrared absorption spectrum of the obtained long-chain alkyl group-containing betaine compound 6 are shown in FIG. 17 and FIG. 18, respectively.

FIG. 17 indicates a peak assignable to the methine group derived from propylene oxide at 4.1 to 4.2 ppm, which represents a chemical shift of about 0.1 ppm from the peak (around 4.0 ppm) of unreacted propylene oxide. FIG. 18 indicates not only the disappearance of the OH-stretching vibrations at 3300 to 3400 cm$^{-1}$ but also the disappearance of the CO$_2$—H stretching vibrations due to the carboxyl group of unreacted cocoalkyl-carboxylic acid around 2550 to 2600 cm$^{-1}$.

The above data indicate the formation of a long-chain alkyl group-containing betaine compound of the following formula (15):

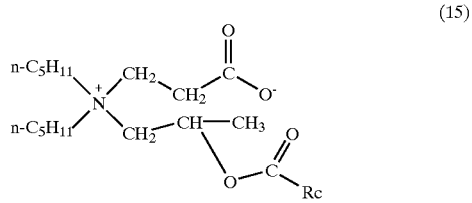
(15)

wherein Rc is as defined hereinbefore.

EXAMPLE 10

Synthesis of 3-(N.N-di-n-Butyl-N-(2-hydroxy) dodecyl ammoniopropanoate [Hydroxy-containing Betaine Compound 4]

A 100 ml four-necked flask equipped with a stirrer, condenser and thermometer was charged with 12 g (0.0596 mol) of the N, N-di-n-butyl-β-alanine obtained in Reference Example 1, 11 g (0.0596 mol) of 1,2-epoxydodecane as the monooxirane, and 30 g of toluene as the solvent, followed by nitrogen purging at room temperature for 10 minutes. Then, the reaction was carried out under heating on an oil bath at 120° C. with constant stirring for 6 hours. The introduction of nitrogen gas was continued so that the reaction was carried through in a nitrogen stream. After the reaction mixture was cooled to room temperature, it was transferred to a 300 ml eggplant-shaped flask and the toluene was distilled off using a rotary evaporator to recover about 22.7 g (yield 98.7%) of a hydroxyl group-containing betaine compound according to the present invention, namely 3-(N, N-di-n-butyl-N-(2-hydroxy)dodecylammoniopropanoate [hydroxy-containing betaine compound 4].

Figure 19:
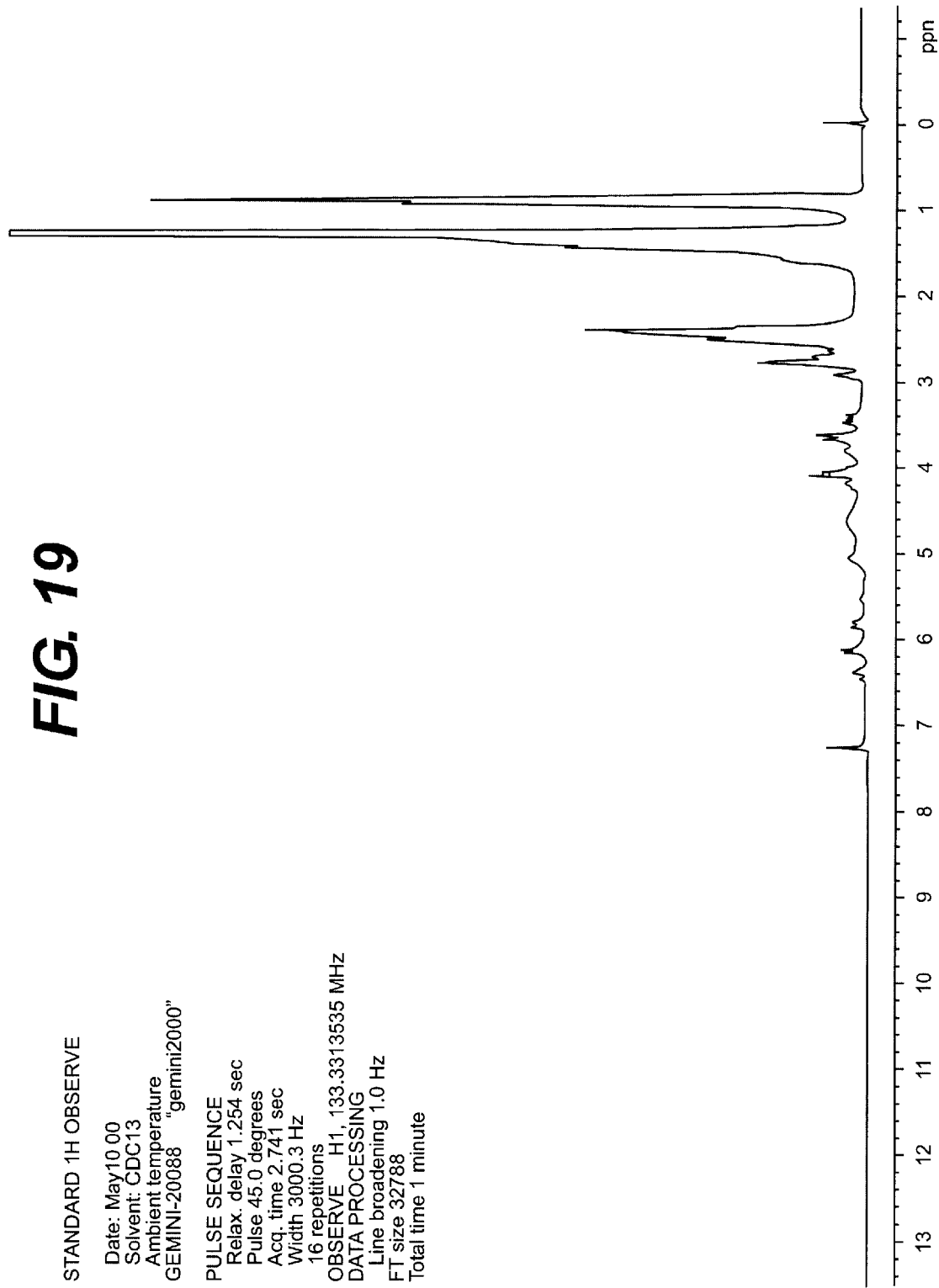
FIG. 19 is a $^1$H-nuclear magnetic resonance spectrum of the hydroxyl group-containing betaine compound 4 obtained in Example 10.
Figure 20:
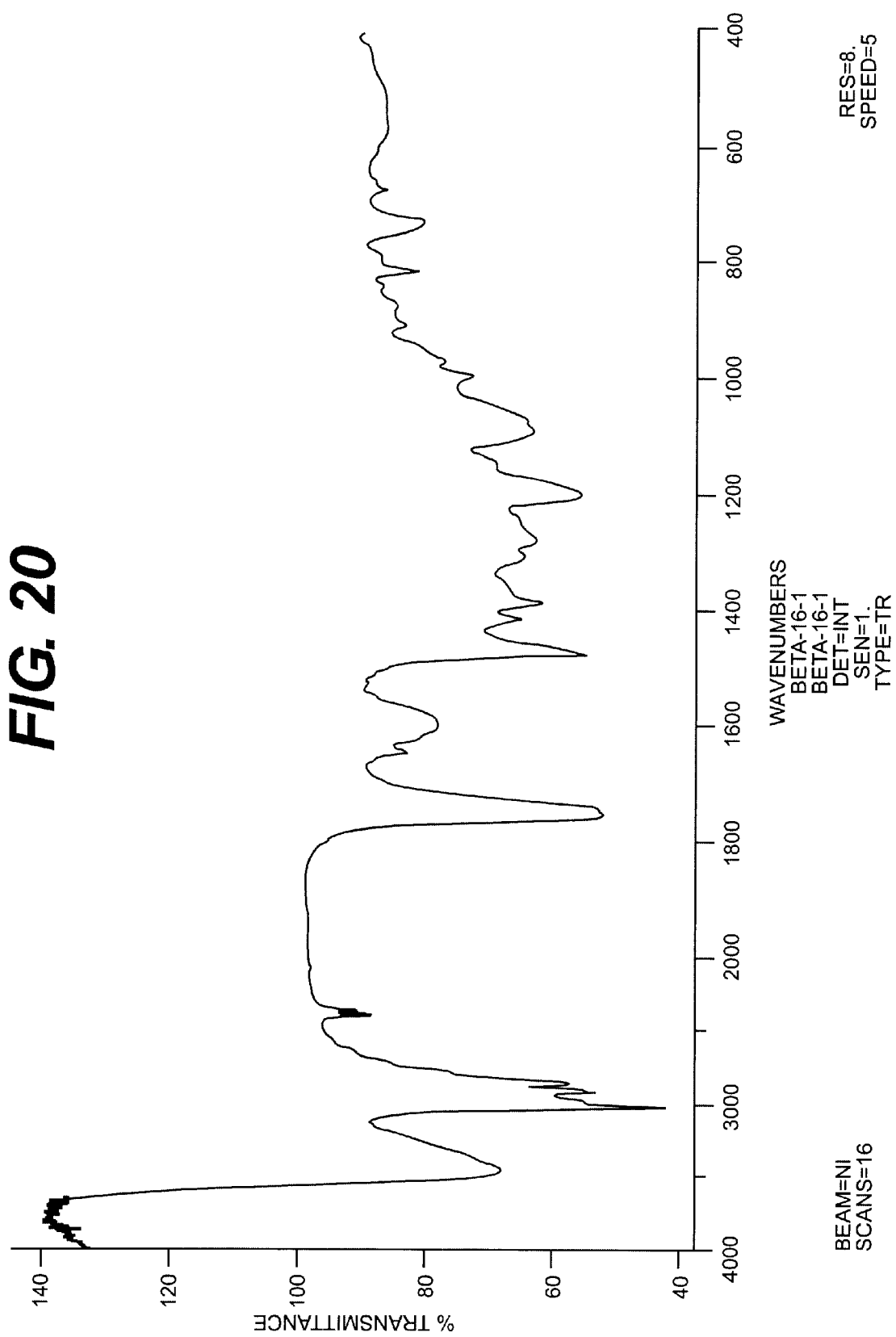
FIG. 20 is an infrared absorption spectrum of the hydroxyl group-containing betaine compound 4 obtained in Example 10.

The $^1$H-nuclear magnetic resonance spectrum and infrared absorption spectrum of the obtained hydroxy-containing betaine compound 4 are shown in FIG. 19 and FIG. 20, respectively.

FIG. 19 shows a peak assignable to the methine group derived from 1,2-epoxydodecane at 4.2 ppm, which represents a chemical shift of about 1.2 ppm from the peak (around 3.0 ppm) of unreacted 1,2-epoxydodecane. FIG. 20 indicates the disappearance of the absorption (2550 to 2600 cm$^{-1}$) of the starting material N,N-di-n-butyl-β-alanine. In addition, there were observed the absorptions of —CH$_2$—N$^+$ and —CH—OH formed de novo around 950 cm$^{-1}$, 1090 cm$^{-1}$ and 1200 cm$^{-1}$ as well as OH-stretching vibrations at 3300 to 3500 cm$^{-1}$.

The above data indicate the formation of a hydroxy-containing betaine compound 4 of the following formula (16).

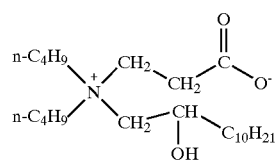

(16)

EXAMPLE 11

Synthesis of 3-(N,N-di-(2-Hydroxy)ethyl-N-(2-hydroxy)octyl)ammoniopropanoate [Hydroxy-containing Betaine Compound 5]

A 100 ml four-necked flask equipped with a stirrer, condenser and thermometer was charged with 10 g (0.0564 mol) of the N,N-di-(2-hydroxy)ethyl-β-alanine obtained in Reference Example 3, 20 g of methanol as the solvent, and 0.6 g of triethylamineas thecatalyst, followedbynitrogen-purging at room temperature for 10 minutes. Then, on an oil bath at 80° C., the internal temperature was raised to the reflux point of methanol. When the internal temperature had steadied, a mixture of 7.24 g (0.0564 mol) of 1,2-epoxyoctane as the monooxirane and 10 g of methanol was added dropwise over 20 minutes. After completion of dropwise addition, the reaction was conducted at the reflux temperature of methanol with constant stirring for 10 hours. The reaction was consistently carried through in a stream of nitrogen.

After the reaction mixture was cooled to room temperature, it was transferred to a 300 ml eggplant-shaped flask, and using a rotary evaporator the solvent methanol and catalyst triethylamine were distilled off to recover about 16.4 g (yield 95.1%) of a hydroxyl group-containing betaine compound according to the present invention, namely 3-(N, N-di-(2-hydroxy)ethyl-N-(2-hydroxy)octyl) ammoniopropanoate [hydroxy-containing betaine compound 5].

Figure 21:
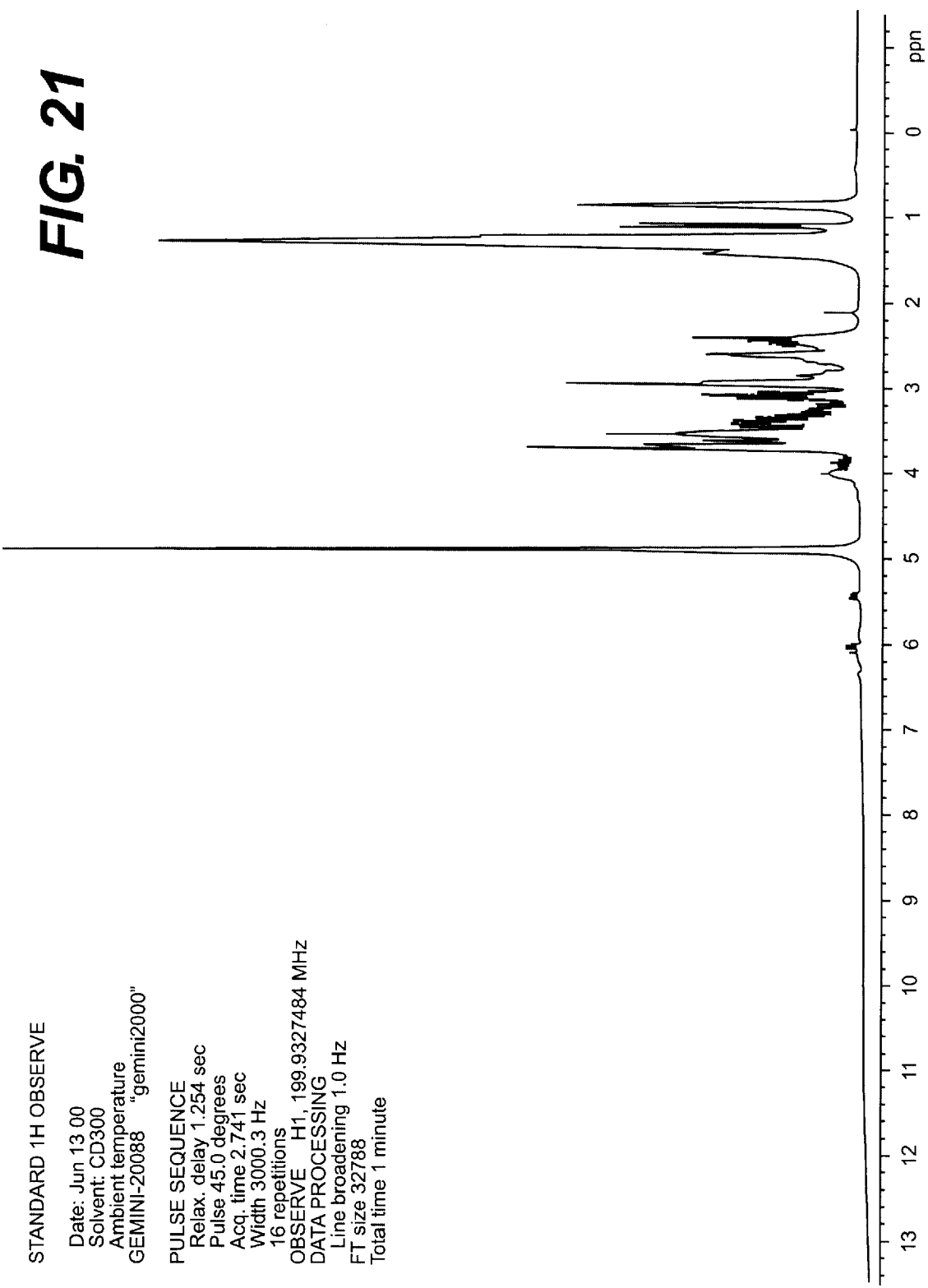
FIG. 21 is a $^1$H-nuclear magnetic resonance spectrum of the hydroxyl group-containing betaine compound 5 obtained in Example 11.
Figure 22:
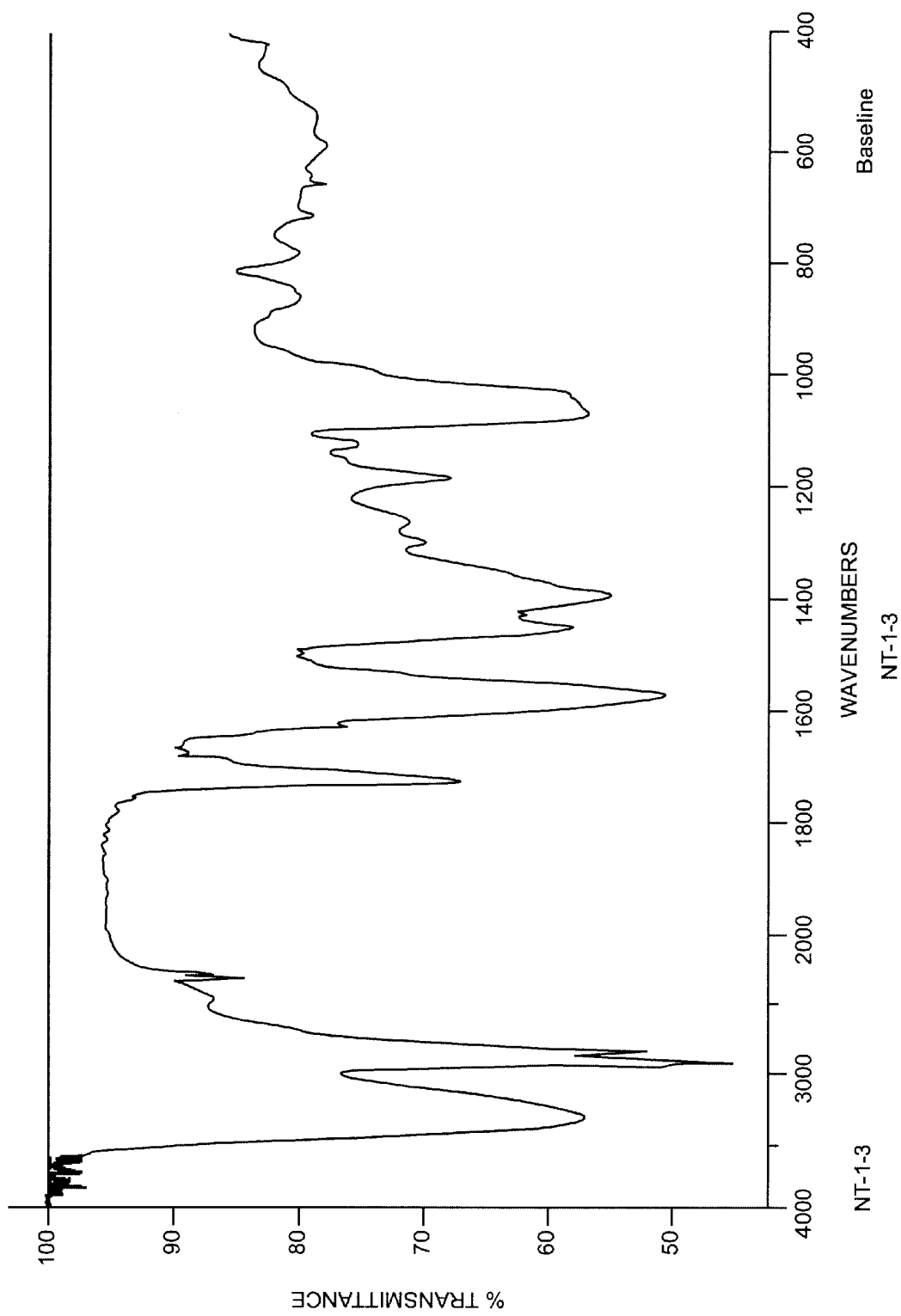
FIG. 22 is an infrared absorption spectrum of the hydroxyl group-containing betaine compound 5 obtained in Example 11.

The $^1$H-nuclear magnetic resonance spectrum and infrared absorption spectrum of the obtained hydroxy-containing betaine compound 5 are shown in FIG. 21 and FIG. 22, respectively.

FIG. 21 shows a peak assignable to the methine group derived from the 1,2-epoxyoctane at 4.1 ppm, which represents a chemical shift of about 1.2 ppm from the peak (around 2.9 ppm) of unreacted 1,2-epoxyoctane. FIG. 22 indicates the disappearance of the absorption (2550 to 2600 cm$^{-1}$) of an amino group in the starting material N,N-di-(2-hydroxy)ethyl-β-alanine. In addition, there were observed the absorptions of —CH$_2$—N$^+$ and —CH—OH formed de novo around 1040 cm$^{-1}$, 1080 cm$^{-1}$ and 1200 cm$^{-1}$ as well as OH-stretching vibrations at 3300 to 3400 cm$^{-1}$.

The above data indicate the formation of a hydroxy-containing betaine compound 5 of the following formula (17).

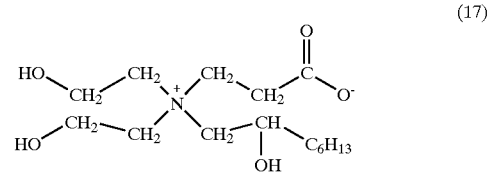

(17)

What is claimed is:

1. A hydroxyl group-containing betaine compound of the following general formula (1):

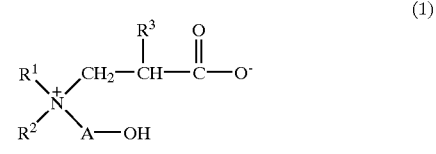

(1)

wherein R$^1$ and R$^2$ may be the same or different and each represents a C$_{2-8}$ hydrocarbon group or a C$_{1-8}$ hydrocarbon group having a hydroxyl group, R$^1$ and R$^2$ may be joined to each other through a single bond or through at least one kind of element selected from the group consisting of O, S and N; R$^3$ represents a hydrogen atom, a methyl group or a hydroxymethyl group; A represents a C$_{2-25}$ hydrocarbon group.

2. A process for producing a hydroxyl group-containing betaine compound of the following general formula (1):

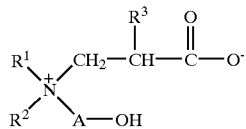

(1)

wherein $R^1$ and $R^2$ may be the same or different and each represents a $C_{2-8}$ hydrocarbon group or a $C_{1-8}$ hydrocarbon group having a hydroxyl group, $R^1$ and $R^2$ may be joined to each other through a single bond or through at least one kind of element selected from the group consisting of O, S and N; $R^3$ represents a hydrogen atom, a methyl group or a hydroxymethyl group; A represents a $C_{2-25}$ hydrocarbon group, which comprises a step of reacting β-alanine derivative of the following general formula (2):

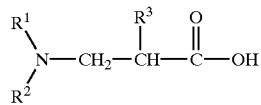

(2)

wherein $R^1$, $R^2$ and $R^3$ are as defined above, with a monooxirane compound.

3. A long chain-alkyl group-containing betaine compound of the following general formula (3):

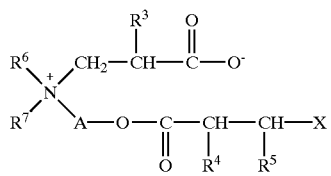

(3)

wherein $R^6$ and $R^7$ may be the same or different and each represents a hydrogen atom or a $C_{1-8}$ hydrocarbon group, exclusive of the case in which both of $R^6$ and $R^7$ respectively represent a hydrogen atom; in case neither $R^6$ nor R7 represents a hydrogen atom, $R^6$ and $R^7$ may be joined to each other through a single bond or through at least one kind of element selected from the group consisting of O, S and N; $R^3$ represents a hydrogen atom, a methyl group or a hydroxymethyl group; A represents a $C_{2-25}$ hydrocarbon group; $R^4$ and $R^5$ are such that whichever one of them represents a hydrogen atom and the other represents a $C_{5-30}$ hydrocarbon group; X represents a hydrogen atom or —COOM, where M represents a hydrogen atom, a metal atom or an ammonium group.

4. A process for producing a long-chain alkyl group-containing betaine compound of the following general formula (3):

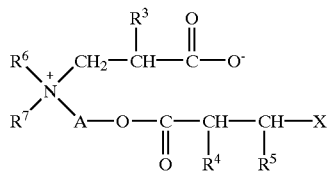

(3)

wherein $R^6$ and $R^7$ may be the same or different and each represents a hydrogen atom or a $C_{1-8}$ hydrocarbon group, exclusive of the case in which both of $R^6$ and $R^7$ respectively represent a hydrogen atom; in case neither $R^6$ nor $R^7$ represents a hydrogen atom, $R^6$ and $R^7$ may be joined to each other through a single bond or through at least one kind of element selected from the group consisting of O, S and N; $R^3$ represents a hydrogen atom, a methyl group or a hydroxymethyl group; A represents a $C_{2-25}$ hydrocarbon group; $R^4$ and $R^5$ are such that whichever one of them represents a hydrogen atom and the other represents a $C_{5-30}$ hydrocarbon group; X represents a hydrogen atom or —COOM, where M represents a hydrogen atom, a metal atom or an ammonium group, which comprises a step of reacting a hydroxyl group-containing betaine compound of the following general formula (6):

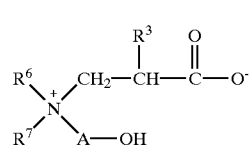

(6)

wherein $R^6$, $R^7$, $R^3$ and A are as defined above, with either a long-chain alkyl group-containing carboxylic acid of the following general formula (4):

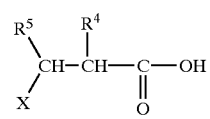

(4)

wherein $R^4$, $R^5$ and X are as defined above, or a long-chain alkyl group-containing carboxylic anhydride of the following general formula (5):

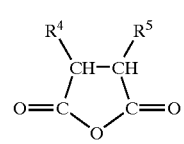

(5)

wherein $R^4$ and $R^5$ are as defined above.

5. The process for producing the hydroxyl group-containing betaine compound according to claim 2, wherein the process comprises a step of synthesizing the β-alanine derivative, and wherein said step is carried out by the addition reaction of an (meth)acrylic acid compound to a primary or secondary amine.

6. The process for producing the hydroxyl group-containing betaine compound according to claim 5, wherein the step of synthesizing the β-alanine derivative is carried out by using a polymerization inhibitor.

* * * * *

UNITED STATES PATENT AND TRADEMARK OFFICE
CERTIFICATE OF CORRECTION

PATENT NO. : 6,452,030 B1
DATED : September 17, 2002
INVENTOR(S) : Chosa et al.

It is certified that error appears in the above-identified patent and that said Letters Patent is hereby corrected as shown below:

Column 21,
Line 17, "P-alanine" change to -- β-alanine --

Signed and Sealed this

Thirteenth Day of May, 2003

JAMES E. ROGAN
*Director of the United States Patent and Trademark Office*